(12) United States Patent
VanDelden

(10) Patent No.: US 11,844,671 B2
(45) Date of Patent: *Dec. 19, 2023

(54) NANO-ENHANCED WOUND DRESSING

(71) Applicant: ULTRAMEND, INC., Ramsey, NJ (US)

(72) Inventor: Jay VanDelden, Trumansburg, NY (US)

(73) Assignee: ULTRAMEND, INC., Ramsey, NJ (US)

( * ) Notice: Subject to any disclaimer, the term of this patent is extended or adjusted under 35 U.S.C. 154(b) by 824 days.

This patent is subject to a terminal disclaimer.

(21) Appl. No.: 16/110,783

(22) Filed: Aug. 23, 2018

(65) Prior Publication Data

US 2019/0091071 A1    Mar. 28, 2019

Related U.S. Application Data

(63) Continuation of application No. 14/301,118, filed on Jun. 10, 2014, now Pat. No. 10,058,455.

(Continued)

(51) Int. Cl.
*A61F 13/00* (2006.01)
*A61K 9/00* (2006.01)
(Continued)

(52) U.S. Cl.
CPC .. *A61F 13/00021* (2013.01); *A61F 13/00991* (2013.01); *A61F 13/00063* (2013.01); *A61F 2013/00327* (2013.01)

(58) Field of Classification Search
CPC ................ A61F 13/00; A61F 13/00021; A61F 13/00991; A61F 13/00063;
(Continued)

(56) References Cited

U.S. PATENT DOCUMENTS 3,800,792 A    4/1974  McKnight et al.
4,886,505 A    12/1989 Haynes et al.
(Continued)

FOREIGN PATENT DOCUMENTS

DE        10309558        9/2004
EP       1997952 B1       5/2008
(Continued)

OTHER PUBLICATIONS

Anselme et al., "Role of materials surface topography on mammalian cell response", International Materials Reviews, vol. 56, No. 4, p. 243 (2011).
(Continued)

*Primary Examiner* — Catharine L Anderson
*Assistant Examiner* — Ilya Y Treyger
(74) *Attorney, Agent, or Firm* — Klintworth & Rozenblat IP LLP

(57) ABSTRACT

The present disclosure relates to a dermal drug delivery platform comprising: a primary wound dressing comprising three-dimensional polymer protuberances that extend upward from the dressing surface to engage the wound. The protuberances comprise at least one biocompatible and/or biodegradable polymer and medicinal nanoparticles. In one embodiment, the medicinal nanoparticles may be metallic and provide surface-area-enhanced galvanic action to drive medicinal ions into the wound bed. Various methods of making the disclosed dermal drug delivery platform, as well as three-dimensional methods of treating a wound using the platform are also disclosed.

12 Claims, 7 Drawing Sheets

Related U.S. Application Data

(60) Provisional application No. 61/956,479, filed on Jun. 10, 2013.

(51) Int. Cl.
*A61K 31/70* (2006.01)
*A61K 9/51* (2006.01)

(58) Field of Classification Search
CPC . A61F 2013/00327; A61K 9/00; A61K 37/00; A61K 31/70; A61K 31/71; A61K 9/51
See application file for complete search history.

(56) References Cited

U.S. PATENT DOCUMENTS

| | | | |
|---|---|---|---|
| 5,685,837 | A | 11/1997 | Hortsmann |
| 5,695,857 | A | 12/1997 | Burrell et al. |
| 5,741,224 | A | 4/1998 | Milder et al. |
| 5,782,788 | A | 7/1998 | Widemire |
| 5,814,094 | A | 9/1998 | Becker et al. |
| 5,837,275 | A | 11/1998 | Burrell et al. |
| 6,080,490 | A | 6/2000 | Burrell et al. |
| 6,160,196 | A | 12/2000 | Knieler et al. |
| 6,333,093 | B1 | 12/2001 | Burrell et al. |
| 6,365,220 | B1 | 4/2002 | Burrell et al. |
| 6,907,294 | B2 | 6/2005 | Andino et al. |
| 7,457,667 | B2 | 11/2008 | Skiba |
| 7,462,753 | B2 | 12/2008 | Ma et al. |
| 7,495,146 | B2 | 2/2009 | Crisp |
| 7,901,711 | B1 | 3/2011 | Sung |
| 7,988,984 | B2 | 8/2011 | Hockaday |
| 8,093,444 | B2 | 1/2012 | Flick |
| 8,143,042 | B2 | 3/2012 | Bettinger et al. |
| 8,293,964 | B2 | 10/2012 | Becker et al. |
| 8,764,681 | B2 | 7/2014 | Aria |
| 8,834,447 | B2 | 9/2014 | Chen |
| 2004/0030276 | A1 | 2/2004 | Flick |
| 2004/0049145 | A1 | 3/2004 | Flick |
| 2005/0244484 | A1 | 11/2005 | Flick |
| 2006/0198903 | A1 | 9/2006 | Storey et al. |
| 2009/0053290 | A1 | 2/2009 | Sand |
| 2010/0069813 | A1 | 3/2010 | Crisp |
| 2014/0005606 | A1 | 1/2014 | Chen |
| 2014/0107740 | A1 | 4/2014 | Crisp |

FOREIGN PATENT DOCUMENTS

| | | |
|---|---|---|
| GB | 1588933 | 4/1981 |
| WO | WO 2007/046806 | 4/2007 |

OTHER PUBLICATIONS

Berger, "Antifungal Properties of Electrically Generated Metallic Ions", *Antimicrobial Agents and Chemotherapy*, vol. 10, No. 5, Nov. 1976, p. 856.
Berger, Electronically generated silver ions: quantitative effects on bacterial and mammalian cells, Antimicrobial Agents and Chemotherapy, vol. 9(2) (1976) pp. 357-358.
Biazar et al., "Cellular orientation on micro-patterned biocompatible PHBV film", *Journal of Paramedical Sciences*, vol. 1, No. 4, 2010, p. 74-77.
Cao et al., "Biological actions of silver nanoparticles embedded in titanium controlled by micro-galvanic effects", Biomaterials, vol. 32, Issue 3, Jan. 2011, pp. 693-705.
Castellano et al., "Comparative evaluation of silver-containing antimicrobial dressings and drugs", Int. Wound J., Blackwell Publishing, vol. 4(2), (2007) pp. 114-122.
Chen et al., "Geometric Control of Cell Life and Death", *Science*, vol. 276, May 1997, p. 1425-1428.
Chou et al., "Imprint of sub-25 nm vias and trenches in polymers", *Applied Physics Letters*, vol. 67, p. 3114, 1995.
Chou et al., "Nanoimprint lithography", J. Vac. Sci. Technol. B, vol. 14(6), (1996) pp. 4129-4133.
Entcheva, "Acoustic micromachining of three-dimensional surfaces for biological applications", Lab Chip. Feb. 2005;5(2):179-83. Epub Nov. 22, 2004.
Foulds et al. "Human Skin Battery Potentials and Their Possible Role in Wound Healing", *British Journal of Dermatology*, vol. 109, p. 515, 1983.
Green et al., "Fibroblast response to microtextured silicone surfaces: Texture orientation into or out of the surface", *Journal of Biomedical Materials Research*, vol. 28, pp. 647-653, 1994.
Guo, L. Jay, "Nanoimprint Lithography: Methods and Material Requirements", Advanced Materials, vol. 19 (2007), pp. 495-513.
Kim et al., "Wound Dressings for Wound Healing and Drug Delivery", Tissue Engineering and Regenerative Medicine, vol. 8, No. 1 pp. 1-7 (2011).
Kwak et al., "Rational Design and Enhanced Biocompatibility of a Dry Adhesive Medical Skin Patch", Advanced Materials, vol. 23 (2011) pp. 3949-3953.
Groenendaal et al., "Poly(3,4-ethylenedioxythiophene) and Its Derivatives: Past, Present, and Future", Advanced Materials, vol. 12, No. 7 (2000) pp. 481-494.
Mahdavi et al., "A biodegradable and biocompatible gecko-inspired tissue adhesive", PNAS, vol. 105, No. 7, (2008) pp. 2307-2312.
Marmaras et al., "Topography-mediated apical guidance in epidermal would healing", Soft matter, vol. 8, p. 6922 (2012).
Martines et al., "Superhydrophobicity and Superhydrophilicity of Regular Nanopatterns", *Nano Letters*, vol. 5, No. 10, pp. 2097-2103, 2005.
McKhann et al., "Oligodynamic Action of Metallic Elements and of Metal Alloys on Certain Bacterial and Viruses", *Pediatrics*, vol. 2, p. 272, 1948.
Nijst et al., "Synthesis and Characterization of Photocurable Elastomers from Poly(glycerol-co-sebacate)", *Biomacromolecules*, vol. 8, No. 10, p. 3067, Oct. 2007.
Nuccitelli, Richard, "A Role for Endogenous Electric Fields in Wound Healing", Current Topics in Developmental Biology, Elsevier, Inc., vol. 58 (2003) pp. 1-26.
Pawar et al., "Preparation, optimisation and characterisation of novel wound healing film dressings loaded with streptomycin and diclofenac", Colloids and Surfaces B: Biointerfaces, vol. 102 (2013) pp. 102-110.
Rajput et al., "Cell interaction study method using novel 3D silica nanoneedle gradient arrays", *Colloids and Surfaces B: Biointerfaces*, vol. 102, p. 111, 2013.
Ramadan et al., "Effect of low-intensity direct current on the healing of chronic wounds: a literature review", J. of Wound Care, vol. 17 (7), pp. 292-296, 2008.
Rizzello et al., "Nanotechnology tools for antibacterial materials", Nanomedicine (Lond). May 2013; 8(5):807-21.
Roach et al., "Progress in superhydrophobic surface development", Soft Matter, vol. 4 (2008) pp. 224-240.
Rovensky et al., "Morphogenetic response of cultured normal and transformed fibroblasts, and epitheliocytes, to a cylindrical substratum surface: Possible role for the actin filament bundle pattern", *Journal of Cell Science*, vol. 107, p. 1255-1263 (1994).
Sant et al., "Nanostructure, dissolution and morphology characteristics of microcidal silver films deposited by magnetron sputtering", Acta Biomaterialia, vol. 3, Issue 3, May 2007, pp. 341-350.
Scheer, Hella-Christin, "Pattern definition by nanoimprint", Proc. of SPIE, vol. 8428 (2012), p. 842802-1.
Shinohara et al., Fabrication of a Polymer High-Aspect-Ratio Pillar Array using UV Imprinting, Micromachines, vol. 4, p. 157-167, 2013.
Spadaro, "Antibacterial Effects of Silver Electrodes with Weak Direct Current", *Antimicrobial Agents and Chemotherapy*, vol. 6, No. 5, Nov. 1974, p. 637-642.
Thurman et al., "The Molecular Mechanisms of Copper and Silver Ion Disinfection of Bacteria and Viruses", CRC Critical Reviews in Environmental Control, vol. 18, issue 4, 1989.
Von Nageli, "On the Oligodynamic Phenomena of Living Cells", *Denkschriften der Schweizerischen Naturforschenden Gesellschaft*, vol. 33, No. 1, p. 174, 1893.

(56) References Cited

OTHER PUBLICATIONS

Wang et al., "A tough biodegradable elastomer", Nature Biotechnology, vol. 20 (2002).
Weiss et al., "Electrical Stimulation and Wound Healing", *Archives of Dermatology*, vol. 126, Feb. 1990, pp. 222-225.
Wheeler et al., "Neural Considerations in the Healing of Ulcerated Tissue by Clinical Electrotherapeutic Application of Weak Direct Current: Findings and Theory", in Reynolds DV, Sjoberg AE, eds., *Neuroelectric Research*, Springfield, Ill: Charles C Thomas, Publisher; pp. 83-89, 1971.
Winter, "Movement of Epidermal Cells Over the Wound Surface", in *Advances in Biology of the Skin*, vol. 5, p. 113-127, 1964.
Wu et al., "Surfactant-free poly(lactide-co-glycolide) honeycomb films for tissue engineering: relating solvent, monomer ratio and humidity to scaffold structure", *Biotechnology Letters*, vol. 33, No. 2, p. 423, 2010.
Xie et al., "Noninvasive Neuron Pinning with Nanopillar Arrays", NanoLetters, vol. 10, (2010) pp. 4020-4024.

Silver containing micropillars

Zinc containing micropillars

NANO-ENHANCED WOUND DRESSING

This application claims the benefit of priority under 35 USC 119(e) to Application No.: 61/956,479, filed on Jun. 10, 2013, which is herein incorporated by reference in its entirety.

BACKGROUND

Wound dressings, or simply dressings, are quantitatively characterized by a number of different parameters such as their: geometry (e.g., size, shape, number of layers and thickness of each layer), material composition (e.g., of each layer, including the use of polymer coatings, etc), conformality (e.g., their ability to conform to the topography of the skin surface), mechanical properties (e.g., tensile strength, elasticity), surface properties (e.g., flat, dimpled, textured, etc), moisture management (e.g., wicking, wetting, moisture penetration, hydrophilic, hydrophobic, evaporation, etc), mode of sterilization, anti-microbial, anti-fungal and/or antibiotic properties, air permeation, vapor permeation, vacuum compatibility, hypoallergenic properties, textile properties (e.g., thread count, warp, weft, weave, cutting properties (edge fraying), etc), infused medicinal content (if any), color, ergonomics, mean time to replacement and the various adhesion mechanisms used for holding them in place, among other things.

A long-standing goal of the medical community in general is to select these various dressing parameters to minimize the "mean time to wound healing" (MTWH) for a highly diverse population of patients, with a highly diverse set of wound conditions, all-the-while adhering stringently to any and all Rules & Regulations imposed by the Food and Drug Administration (FDA), and to implement high-volume manufacturing methods that would enable inexpensive world-wide accessibility.

Traditionally, dressings were made of gauze pads or bandages made from natural and/or synthetic materials wherein wound exudate would be absorbed by the dressing to keep the wound dry and to help prevent the ingress of harmful bacteria. More recently, however, it has been shown that wounds heal faster and more efficiently when they are kept moist.

It has been known for many years that certain metals possess anti-microbial, anti-bacterial, anti-fungal, anti-biotic and/or other medicinal properties when introduced into a wound system (see for example, Von Nageli, "On the Oligodynamic Phenomenon in Living Cells", *Denkschriften der Schweizerischen Naturforschenden Gesellschaft*, Vol. 33, No. 1, p.174, 1893 and McKhann, Carlson, and Douglas, "Oligodynamic Action of Metallic Elements and of Metal Alloys on Certain Bacterial and Viruses", *Pediatrics*, Vol. 2, p.272, 1948). These metals include: silver (Ag), gold (Au), platinum (Pt), palladium (Pd), copper (Cu), and zinc (Zn), among others. Of these, however, silver is perhaps the best known.

Anodic silver at low direct currents is known to have inhibitory, anti-bacterial and/or anti-fungal properties. See for example, Berger, ("Antifungal Properties of Electrically Generated Metallic Ions", *Antimicrobial Agents and Chemotherapy*, Vol. 10, No. 5, Nov. 1976, p.856) and Spadaro ("Antibacterial Effects of Silver Electrodes with Weak Direct Current", *Antimicrobial Agents and Chemotherapy*, Vol. 6, No. 5, Nov. 1974, p.637).

Additionally descriptive of antimicrobial surfaces comprising two or more metals in contact with a body electrolyte that produces galvanic action is U.S. Pat. No. 4,886,505 to Haynes et al. Other patents which describe galvanic cells and galvanic elements, include U.S. Pat. No. 5,685,837, Horstmann; and U.S. Pat. No. 6,365,220 to Burrell, which are incorporated by reference herein. However, prior art approaches are lacking in numerous respects. For example, Burrell's approach requires multiple evaporations of different metals and subsequent metal etching techniques that, more-often-than-not, require the use of highly corrosive chemicals and/or toxic gas plasmas (such as chlorine and/or fluorine). More importantly, nowhere in Burrell's work does he mention the use of metallic anti-microbial nanospheres suspended in an array of biodegradable polymer nano and/or micropillars.

U.S. Pat. No. 7,457,667 to Skiba, which is also incorporated by reference, describes a current-producing wound dressing but does not suggest using micropillars to increase the contact surface area between the wound electrolyte and the galvanic surface. Skiba also fails to mention the important class of biodegradable polymers that can be used for a controlled release of the metallic ions. Instead, he refers only to "biocompatible binders" that are used in making the inks. Skiba describes a more traditional surface effect to wound healing. This can be considered a two-dimensional approach to wound healing because the ink described in this reference is in proximal contact with the wound surface, and is not inserted into a wound, which can be considered a three-dimensional approach to wound healing. For example, in a three dimensional approach to wound healing, protuberances or pillars are actually inserted into the wound for a three dimensional response.

SUMMARY

To the best of applicant's knowledge, nowhere in the prior art has anyone utilized a wound dressing comprised of patterned biodegradable polymer protuberances with medicinal particles contained therein, as described herein. Such a construct could and/or should allow for: enhanced galvanic action to push more medicinal ions into the wound bed, extracellular scaffolding with preferential/differential cell growth exhibited thereon, and/or better moisture management, for example. Accordingly, there is a pronounced need for incorporating such nanoparticle-containing biodegradable polymer protuberances into a nano-enhanced wound dressing to facilitate, for example, heretofore-unprecedented rates of wound healing along with possible other advantages.

Herein, there is disclosed nano-enhanced wound dressings that employ numerous patterned protuberances with multiple medicinal nanoparticles contained therein to facilitate the healing process when placed into direct contact with the wound. There is also disclosed wound dressings as described, that further employ galvanic action to assist in wound healing. Embodiments described herein include articles, methods of making articles, and methods of using articles.

For example, one embodiment provides a dermal drug delivery platform comprising: a primary wound dressing comprising three-dimensional polymer protuberances that extend upward from the dressing surface to engage the wound, wherein the protuberances comprise at least one biocompatible and/or biodegradable polymer and medicinal nanoparticles.

In one embodiment, the polymer protuberances have a columnar or pillar shape with a base having a longest dimension ranging from 1 μm to 1000 μm, and a cross-section shape that is round, square, rectangular, hexagonal, elliptical, completely general, or combinations thereof.

In another embodiment, the medicinal nanoparticles are metallic and are selected from: silver, gold, copper, zinc, platinum, palladium and/or combinations thereof.

In another embodiment, the wound comprises an electrolyte, and the metallic nanoparticle-containing polymer protuberances are selected to maximize a galvanic response between said protuberances and the electrolyte.

In another embodiment, the medicinal nanoparticles are uniformly distributed within the polymer protuberances. In another embodiment, the medicinal nanoparticles are non-uniformly distributed within the polymer protuberances. In another embodiment, the medicinal nanoparticles have a varying concentration from the tip of the polymer protuberances to the base of the polymer protuberances.

In another embodiment, the medicinal nanoparticles include anti-microbial, anti-fungal, anti-biotic, and/or growth-promoting agents. In another embodiment, the growth-promoting agents comprise Interleukins (IL-6, IL-7, IL-8), Keratinocyte growth factor (KGF) and/or Hepatocyte growth factor (HGF).

In another embodiment, the medicinal nanoparticles are spherical in shape with a diameter ranging from 2 nm to 500 nm.

In another embodiment, the biodegradable polymer comprises PLA, PGA, PEG, PLGA, PGSA, and/or combinations thereof. In another embodiment, the biocompatible polymer is comprised of PEDOT.

In another embodiment, the molecular weight of the polymer in the polymer protuberances is chosen to optimize the controlled release rate of medicinal nanoparticles into the wound. In another embodiment, the spacing and size of the polymer protuberances are selected so as to make the primary dressing surface superhydrophobic.

In another embodiment, the wound dressing further comprises an outer cover and at least one layer located between the primary dressing and the cover.

In another embodiment, the outer cover is comprised of a polymer, chosen from latex, mylar, polyethylene, polypropylene, nylon, rayon and/or combinations thereof.

In another embodiment, the polymer protuberances release the medicinal nanoparticles as a result of a stimulus.

In another embodiment, the stimulus comprises a saline rinse, a change in temperature, sweat or perspiration, wound electrolytes, an electrical field, a magnetic field, or any combination of the foregoing.

In one further embodiment, there is disclosed a dermal drug delivery platform comprising an enhanced wound dressing comprising nanopillars and/or micropillars that extend upward from the dressing surface to engage the wound, and containing non-metallic and/or metallic nanoparticles. When the nanoparticles are metallic, they provide galvanic action when in contact with an electrolyte contained in the wound. While not necessary, the galvanic action can lead to enhanced wound healing via electrical wound stimulation.

Another aspect is a method of making the dermal drug delivery platform comprising: dispersing medicinal nanoparticles in at least one biocompatible and/or biodegradable polymer; and depositing said medicinal nanoparticle containing polymer onto a primary dressing surface to form three-dimensional polymer protuberances.

Another embodiment is further comprises placing one or more secondary layers over the primary dressing on the side opposite the three-dimensional polymer protuberances. Another embodiment comprises placing an outer layer on top of the secondary layers, such that the secondary layers are located between the primary dressing and the outer layer.

In another embodiment, the polymer protuberances comprise multiple-species, and are formed by a method comprising: depositing a first polymer layer containing medicinal nanoparticles onto the primary dressing surface; depositing a second polymer layer containing medicinal nanoparticles overtop of the first polymer layer; depositing a third polymer layer containing medicinal nanoparticles overtop of the second polymer layer; and pressing a heated mold with a complementary pattern of pits against the primary dressing surface and the first, second, and third polymer layers to form a pattern of multiple-specie polymer protuberances.

In another embodiment, the first polymer layer comprises zinc nanoparticles in PLGA; the second polymer layer comprises silver nanoparticles in PLGA; and the third polymer layer comprises anti-microbial agents, anti-fungal agents, anti-biotic agents, germicidal agents, anti-bacterial agents, growth-promoting agents and/or combinations thereof.

In another embodiment, the mold is made from silicon and includes a non-stick layer.

In another embodiment, the polymer protuberances are in the shape of a tapered cone.

In another embodiment, the polymer protuberances are formed by a method comprising: depositing a first polymer layer containing medicinal nanoparticles onto the primary dressing surface; placing a mask over top of and proximal to the first polymer layer, wherein said mask has a pattern with openings to allow light to pass there-through; exposing the first polymer layer to UV light to cure the polymer in the mask openings only, leaving the areas not exposed to UV light uncured; removing the uncured areas of the first polymer layer thereby forming a first pattern of polymer protuberances; depositing a second polymer layer containing medicinal nanoparticles onto the primary dressing surface; placing a mask over top of and proximal to the second polymer layer, wherein said mask has a pattern with openings to allow light to pass there-through; exposing the second polymer layer to UV light to cure the polymer in the mask openings only, leaving the areas not exposed to UV light uncured; removing the uncured areas of the second polymer layer thereby forming a second pattern of polymer protuberances different from the first pattern; depositing a third polymer layer containing medicinal nanoparticles onto the primary dressing surface; placing a mask over top of and proximal to the third polymer layer, wherein said mask has a pattern with openings to allow light to pass there-through; exposing the third polymer layer to UV light to cure the polymer in the mask openings only, leaving the areas not exposed to UV light uncured; removing the uncured areas of the third polymer layer thereby forming a third pattern of polymer protuberances different from both the first pattern and the second pattern.

In one embodiment, at least one of the first, second, or third polymer comprises PGSA.

In one embodiment, the first medicinal nanoparticle comprises silver; the second medicinal nanoparticle comprises zinc; and the third medicinal nanoparticle is selected from anti-microbial agents, anti-fungal agents, anti-biotic agents, germicidal and/or anti-bacterial agents, and/or combinations thereof.

Another embodiment is for a three-dimensional method of treating a wound, said method comprising: covering said wound with the dermal drug delivery platform comprising: a primary wound dressing comprising three-dimensional polymer protuberances that extend upward from the dressing surface to engage the wound, wherein the protuberances comprise at least one biocompatible and/or biodegradable polymer and medicinal nanoparticles, and inserting said polymer protuberances into the wound to make direct contact with the wound.

In one embodiment, the biocompatible and/or biodegradable polymer dissolves in the wound and thereby releases said medicinal nanoparticles into the wound.

In one embodiment, the medicinal nanoparticles facilitate galvanic action between said protuberances and at least one wound electrolyte.

In one embodiment, the medicinal nanoparticles comprise silver, gold, copper, zinc, platinum, palladium and combinations thereof; and the wound exudate comprises an electrolyte.

In one embodiment, the biodegradable polymer is selected from: PLA, PGA, PEG, PLGA and/or PGSA; and the biocompatible polymer is comprised of PEDOT.

BRIEF DESCRIPTION OF THE DRAWINGS

Further features and advantages of the disclosure are shown in the drawings described below, and the detailed description that follows thereafter.

DETAILED DESCRIPTION

Figure 1:
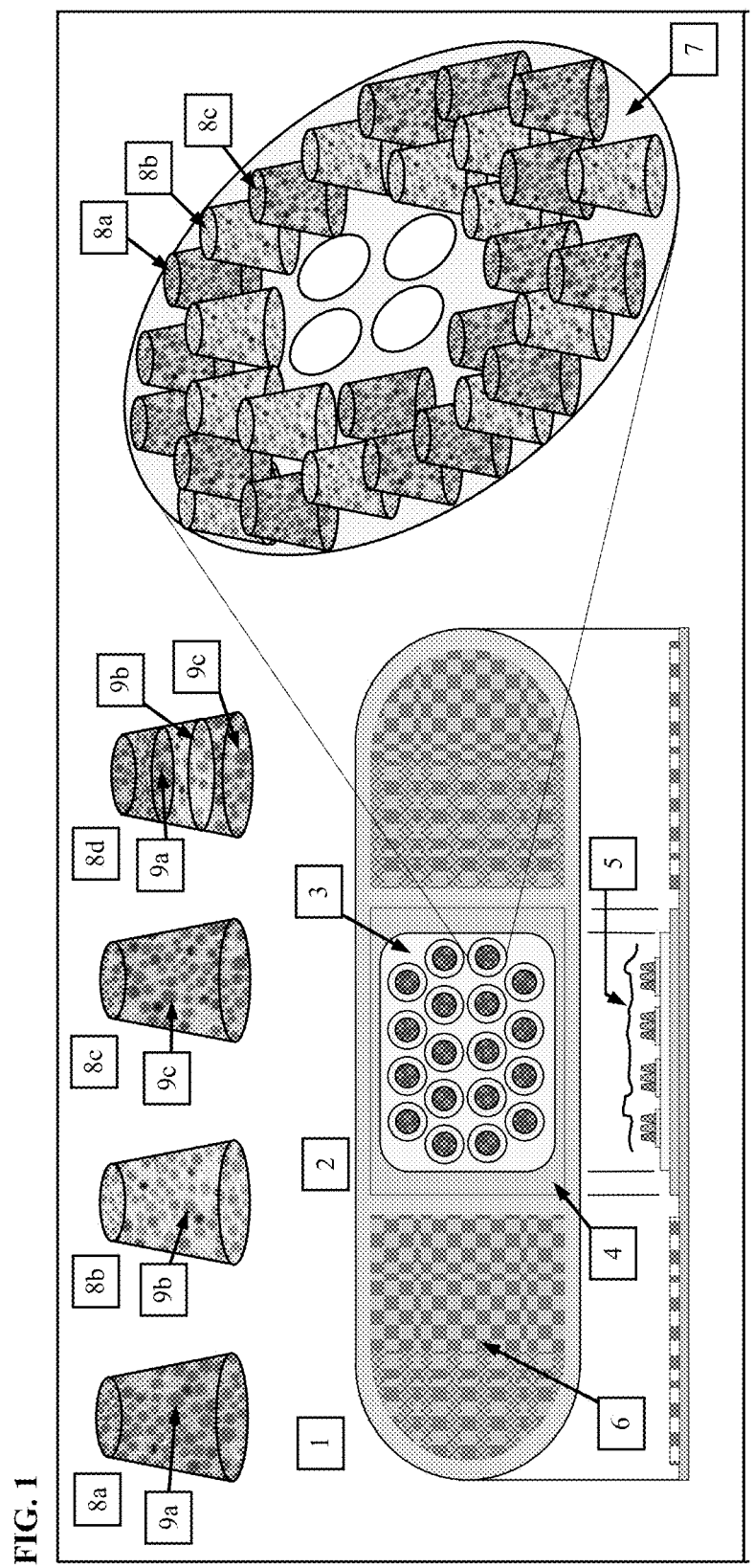
FIG. 1 depicts one embodiment of a nano-enhanced wound dressing system wherein three (3) species of nanoparticle containing, biodegradable, micropillars are spread across the surface of the primary dressing to make it actively anti-microbial.

Definitions:

As used herein and throughout, the term "wound" refers to, but is not limited to, any cut, incision, slash, gash, lesion, laceration, puncture, abrasion, scrape, bruise, crack, trauma, contusion, burn, ulcer, amputation, or tissue damage of any kind, of, or pertaining to, the skin.

Wounds can be quantitatively characterized by a number of different parameters such as their: type (acute versus chronic, open versus closed, etc), lateral extent (including the size and shape of the wound), degree of severity (including the depth into the epidermis or dermis), location (on the body), phase of healing, time lapse since occurrence, volume flow-rate and quality of exudate, pH, moisture (including humidity), electrochemical properties (voltage, current, etc), scab formation (if any), blood flow/vascularization, epithelial growth rate, oxygenation, temperature, condition of the patient (age, health, hydration, hormonal balance, comorbidities, etc), and color (appearance), among other things.

A wound will typically exhibit three (3) overlapping phases during the healing process. During the first phase, the so-called inflammatory phase, both hemostasis (stoppage of bleeding) and phagocytosis (engulfing and ingesting unwanted bacteria or foreign debris) are initiated. During the second phase, the so-called proliferation phase, new blood vessels are formed (angiogenesis), fibroblasts excrete collagen and fibronectin (to form a new extracellular matrix ECM) with granulation, epithelialization and wound contraction resulting. In the last phase, the so-called remodeling phase, collagen production is slowed with greater organization (i.e. alignment along tensile lines) to strengthen the tissue.

As used herein and throughout, the phrase "dermal drug delivery platform" refers to a system to facilitate the healing of a wound by transmitting medicine directly to the wound via an enhanced wound dressing. The enhanced wound dressing can comprise medicinal nanoparticles contained in polymer protuberances that are configured to extend into a wound when the dressing is applied to the skin, and can release their medicinal nanoparticles when the polymer dissolves.

As used herein and throughout, the term "dressing" refers to, but is not limited to, any surface that is brought into direct contact with a wound for purposes of helping to heal the wound or preventing additional harm, including those from infection, contamination, and/or other environmental/physical factors such as bumping, hitting or scratching.

As used herein and throughout, the term "bandage" refers to, but is not limited to a dressing and some means for holding the dressing in place against the skin.

As used herein and throughout, the term "primary dressing" refers to, but is not limited to, a dressing which is placed in direct contact with the wound surface.

As used herein and throughout, the term "secondary dressing" refers to, but is not limited to, a dressing which is in contact with the primary dressing but not necessarily in direct contact with the wound surface. A secondary dressing may, for example, be deployed in-between the primary dressing and the outer covering of the bandage for purposes of moisture management.

As used herein and throughout, the term "exudate" or "wound exudate" (also sometimes called wound "drainage") refers to, but is not limited to the natural liquid produced by the body in response to tissue damage. Wound exudate bathes the wound (i.e. keeps it moist) and supplies vital nutrients to the wound bed thereby facilitating optimal healing conditions.

As used herein and throughout, the term "anti-microbial surface" refers to, but is not limited to, those surfaces that are useful in avoiding, preventing and/or treating bacterial, fungal and/or microbial infections by releasing certain substances (aka anti-bacterial, anti-fungal and/or anti-bacterial substances) that are effective at suppressing the growth of such organisms.

As used herein, the phrase "galvanic action" refers to the movement of electrons and ions that occurs when two electrochemically dissimilar metals are immersed in an electrolyte. One non-limiting example of galvanic action occurs when cathode-like metals, such as silver, and anode like metals, such as zinc, are immersed in wound electrolyte. This method of introducing metallic ions into the wound system is particularly useful because it does not require an external power supply.

As used herein and throughout, the term "nano" refers to one-billionth ($1 \times 10^{-9}$) of the unit of measure that follows. For example, there are one-billion nanometers (nm) in one meter and 1000 nanometers (nm) in a micron (µm).

As used herein and throughout, the term "micro" refers to one-millionth ($1 \times 10^{-6}$) of the unit of measure that follows. For example, there are one-million micrometers (µm) in one meter and 1000 micrometers (µm) in a millimeter (mm). Microns and micrometers shall be used interchangeably.

As used herein and throughout, the term "pillar" refers to a three dimensional structure, such as a column, having an aspect ratio in which the height is greater than both the length and the width.

As used herein, and throughout, the terms "micropillar" and "nanopillar" refers to a "pillar," as defined above, in which the height is either on the micrometer scale (micropillar) or on the nanometer scale (nanopillar).

As used herein and throughout, the term "protuberance" refers to, but is not limited to, any protrusion of any shape that extends upward from the dressing surface to engage the wound. For example, the protuberance may have an elongated rectangular shape to form walls of polymer that extend upward from the primary dressing surface. When viewed in cross-section, this will appear as grooves between each wall structure. In another embodiment, the protuberances may have a column or pillar shape as previously described, wherein the column or pillar has a base with any of a variety of shapes, including but not limited to round, square, rectangular, hexagonal, elliptical, completely general, or combinations thereof.

As used herein and throughout, the "tip" of the polymer protuberance is defined as the distal end of the protuberance. As the tip is farthest away from the primary dressing, it is more likely to engage the wound before any other part of the protuberance.

As used herein and throughout, the "base" of the polymer protuberance is defined as the proximal end of the protuberance. The base of the protuberance is attached to the primary dressing.

As used herein and throughout, the term "hot embossing" refers to a process of stamping a pattern into a polymer layer that has been softened by temporarily raising its temperature above the polymer's glass transition temperature. One non-limiting embodiment of the stamp that can be used is one that is micro-machined out of silicon.

As used herein and throughout, a "hydrophobic surface" is one that is not easily wetted (i.e. one that repels water). Silicon is a hydrophobic material, as are most polymers.

As used herein and throughout, a "hydrophilic surface" is one that is easily wetted (i.e. one that invites water to spread out across the whole surface). Oxide, or more precisely, silicon dioxide, is a hydrophilic surface.

As used herein and throughout a "superhydrophobic surface" is one that exhibits extreme water-repellency, with water droplets that rest upon them with very large contact angles.

A variety of skins and wounds can be treated with the articles and methods described herein. Mammalian skin and wounds therein are common examples. Mammalian skin is comprised of three different layers. The outermost layer (the epidermis) protects the body from the outside environment. Just beneath the epidermis lies the dermis which consists of an extracellular collagen matrix, nerve endings, lymphatic and blood vessels, sweat glands and hair follicles, among other things. Beneath the dermis lies a subcutaneous fat layer which helps to prevent heat loss.

Dermal Drug Delivery Platform

There is disclosed herein a dermal drug delivery platform used as an enhanced wound-healing system to treat these various types of wounds comprising a primary dressing surface comprising biocompatible and/or biodegradable polymer protuberances, wherein a majority of the polymer protuberances comprise medicinal nanoparticles.

The nano-enhanced wound dressing described herein, e.g., with a pattern of protuberances engaging the wound system, provides numerous advantages in wound care over existing dressings including, but not limited to one or more of the following, including combinations thereof:

A nano-enhanced wound dressing in the form of nano and/or micropillars made from (or containing) silver, zinc or other metals, when brought into contact with the wound exudate, will produce galvanic microcurrents for stimulating the wound healing process.

A nano-enhanced wound dressing in the form of nanopillars and/or micropillars made from a biodegradable polymer and containing silver, zinc or other metals will result in a sustained release of these antimicrobial constituents at therapeutic levels. As the polymer dissolves away, the infused metals will be released into the wound in a controlled manner.

A nano-enhanced wound dressing in the form of nanopillars and/or micropillars brought into contact with the wound can (under certain circumstances) provide a fertile "scaffold" for new cells to grow within.

A nano-enhanced wound dressing in the form of nanopillars and/or micropillars brought into contact with the wound can be made to differentiate between "good" cells and "bad" cells.

A nano-enhanced wound dressing according to the present disclosure may allow superhydrophobic wetting properties to be used in the overall moisture management of the wound/dressing system. Superhydrophobic (i.e. highly non-wetting) surfaces do not wick away moisture as in the case of traditional fabrics/textiles. And these wetting properties can be tuned, depending on the details of the nano-textured surface.

A nano-enhanced wound dressing according to the present disclosure may facilitate skin cell growth preferentially faster in one direction than another, to better match the shape of the wound bed.

A nano-enhanced wound dressing according to the present disclosure may facilitate an anesthetic response for the reduction of pain associated with the wound.

A nano-enhanced wound dressing in the form of nanopillars and/or micropillars brought into contact with the wound bed increases the contact area many times (over that of a flat surface) which enhances the galvanic microcurrent and the amount of silver ions that are forced into the wound.

Depending on the molecular weight of the biodegradable polymer used to fabricate the nanopillars and/or micropillars, they can dissolve quickly over time or dissolve more slowly, thus allowing a tunable release rate of the infused metal (silver, zinc, etc) nanoparticles.

A nano-enhanced wound dressing in the form of biodegradable nanopillars and/or micropillars brought into contact with the wound surface is amenable to future medical innovations in that advanced medicinals can be slowly released as a result of the dissolving pillars.

A nano-enhanced wound dressing in the form of biodegradable nanopillars and/or micropillars brought into contact with the wound surface could allow tailored degradation profiles wherein the release of silver ions or the wicking action of the dressing surface can be controlled over a longer period of time.

A nano-enhanced wound dressing according to the present disclosure may benefit persons with poor blood circulation in that the wound will stay optimally moist, with more anti-microbials and an advanced rate of healing due to galvanic microcurrents.

A nano-enhanced wound dressing according to the present disclosure is able to address a larger percentage of the population with an ever-increasing diversity of wound care needs.

A nano-enhanced wound dressing according to the present disclosure is amenable for use on virtually any surface that would come into contact with biological electrolyte material. The nanopillars and/or micropillars can be transferred onto a flat surface, a curved surface (in the case of a catheter) or a fabric surface.

Galvanic action will not begin until after the dressing comes into contact with the wound exudate. Alternatively, it could be activated by sweat (aka perspiration) or a saline rinse. Prior to that, the product will have a long shelf (aka storage) life.

A nano-enhanced wound dressing according to the present disclosure can be made to release various medicinal agents at different rates/times throughout the lifecycle of the dressing and/or healing process. For example, medicinal specie 1 can be released immediately upon placing the dressing in contact with the wound and medicinal specie 2 can be released several days after that. In this way, the dressing can be optimized for the shortest possible overall healing time.

A nano-enhanced wound dressing according to the present disclosure could be designed to release the medicinal constituents in response to body temperature.

A nano-enhanced wound dressing according to the present disclosure could be designed to release the medicinal constituents in response to some other external stimulus, such as an electric field or a magnetic field.

Traditional Adhesive Bandage System

The traditional Adhesive Bandage 11 (see FIG. 2) is comprised of an Adhesive Strip 12 on opposing sides of the Dressing 13. The Dressing 13 can be further comprised of any number of Primary, Secondary, Tertiary, etc . . . , dressing layers.

Wound exudate may include one or more of electrolytes, glucose, cytokines, leukocytes, metalloproteinases, macrophages, platelets, fibrin and micro-organisms, among other things.

Types of wound exudate include: serous (clear, amber, thin and watery), fibrinous (thin and cloudy with strands of fibrin), serosanguineous (clear, pink, thin and watery), sanguineous (reddish, thin and watery), seropurulent (yellow or tan, cloudy and thick), purulent (opaque and milky), hemopurulent (reddish, milky and viscous) and hemorrhagic (red and thick).

Figure 2:
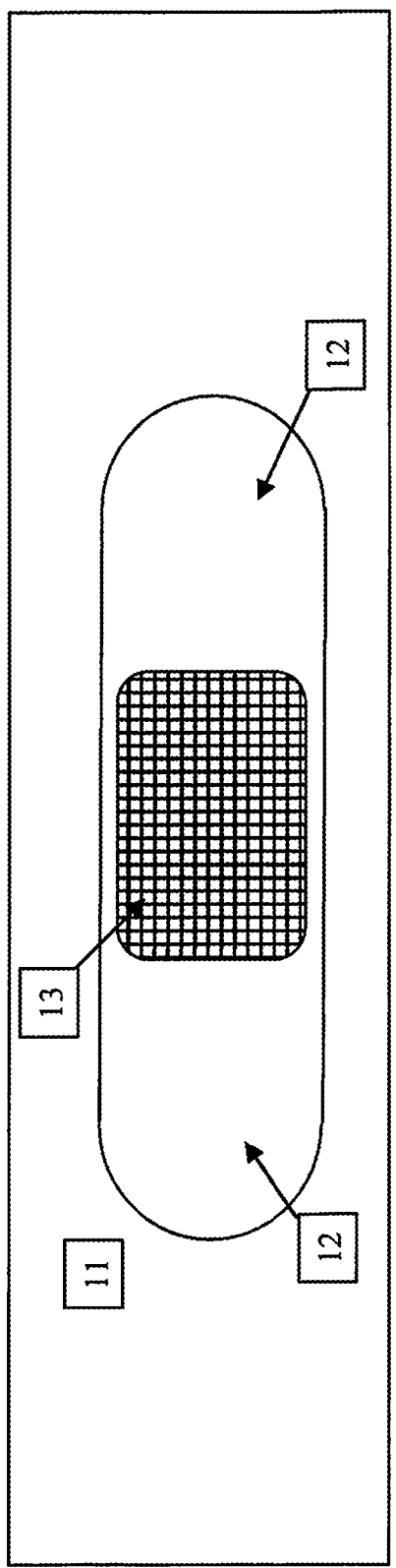
FIG. 2 depicts a conventional, prior art adhesive bandage system with primary dressing and adhesive strip.

With reference to FIG. 2, the Primary Dressing 13 is used to help stop bleeding, absorb blood/wound exudate, ease pain, debride the wound, protect the wound from infection and to generally promote the healing process in whatever way possible, among other things.

The Adhesive Strip 12 is used to secure the Dressing (including the Primary Dressing, the Secondary Dressing and Other Dressing Layers) against the wound. The Adhesive Strip 12 sometimes comes in the form of vinyl tape.

The Primary Dressing 13 can be made of cotton gauze or blended rayon/polyester, among other things. The Primary Dressing 13 often comes in the form of an absorbent pad.

Preferably, but not necessarily, the Primary Dressing is encapsulated within a non-stick coating such as polyethylene terephthalate to prevent the material from sticking to the wound. In such cases, the coated material is perforated to allow fluid to seep into the dressing as needed.

Adhesive Bandages are typically sterilized using Gamma Radiation.

Electrical Potential of Human Skin

Healthy human skin typically exhibits an electrical potential across the epithelium (the transepithelial potential or TEP for short). And, the inner-most workings of this "epidermal battery" are jeopardized in the event of a wound.

As early as 1964, Winter ("Movement of Epidermal Cells Over the Wound Surface", *Advances in Biology of the Skin*, Vol. 5, p.113, 1964) showed that the cells migrating across a wound come from the 0.5 mm wide peripheral region around the wound where substantial voltage gradients exist. He and other researchers at the time suggested that maybe the epithelial cells move under the influence of these voltages, along the direction of current flow. Wheeler et al. ("Neural Considerations in the Healing of Ulcerated Tissue by Clinical Electrotherapeutic Application of Weak Direct Current: Findings and Theory", *Neuroelectric Research*, p. 83, 1971) was arguably the first to suggest that electrical stimulation could be used to encourage wound healing.

In 1983, Foulds et al. ("Human Skin Battery Potentials and Their Possible Role in Wound Healing", *British Journal of Dermatology*, Vol. 109, p.515, 1983) measured an average potential of 23.4 mV (between the stratum corneum and the dermis) at many different locations across the body. He also showed that the palms of the hands (36.9 mV) and soles of the feet (39.0 mV) exhibited consistently higher voltages.

In 1990, Weiss et al. (Archives of Dermatology, Vol. 126, February.1990, P.222) summarized well that electrical stimuli can be used to accelerate the healing process.

Cell Response To Nano-Textured Surfaces

In 1994, Rovensky et al. (*Journal of Cell Science*, Vol. 107, p.1255) showed that cells cultured on cylindrical surfaces with a high degree of curvature affected their size, shape and orientation. In addition, Rovensky and his colleagues discovered that certain cells were more affected than others by this surface geometry.

Also in 1994, Green et al. (*Journal of Biomedical Materials Research*, Vol. 28, p.647, 1994) found that cells exhibited increased rates of proliferation on pillars as compared to equivalent-sized trenches.

In 1997, Chen et al. (*Science*, Vol. 276, May 1997, p.1425) used microcontact printing methods to form circular/square fibronectin-coated islands. They found that endothelial cells would grow until they took on the size and shape of the island, with a marked decrease in apoptosis (cell termination) for larger islands as compared to smaller islands.

In 2012, Rajput et al. (*Colloids and Surfaces B: Biointerfaces*, Vol. 102, P.111, 2013) reported that "when surface topographical features are considerably larger in vertical dimension and are spaced at least one cell dimension apart, the features act as 3D physical barriers that can guide cell adhesion, thereby altering cell behavior".

Figure 4:
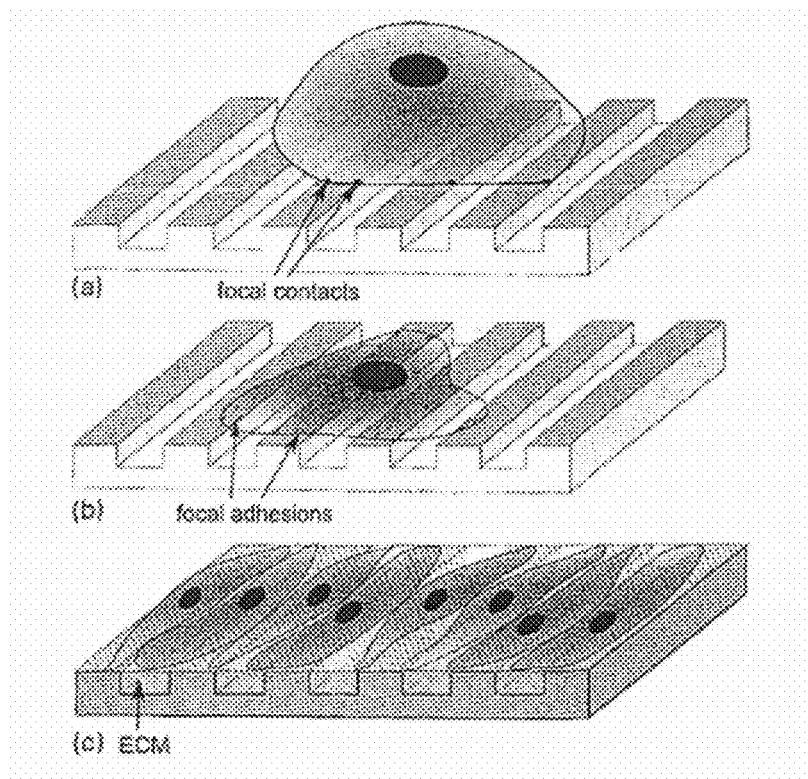
FIG. 4 depicts an image of cellular growth on a surface comprising grooves.

Few researchers would argue that the growth of cells on a surface can depend on the nano-topography of said surface. For example, FIG. 4 shows Cell Attachment and Spreading on a grooved surface.

Surface topography can depend on the: size (length, width, diameter, height) of the features formed thereon, including their cross-sectional shape (square, rectangular, spherical, elliptical, etc), relief tone (hill vs valley), spacing (from peak to peak or valley to valley), sidewall condition (straight, reentrant, sloped, tapered, etc), among many other things.

Figure 3:
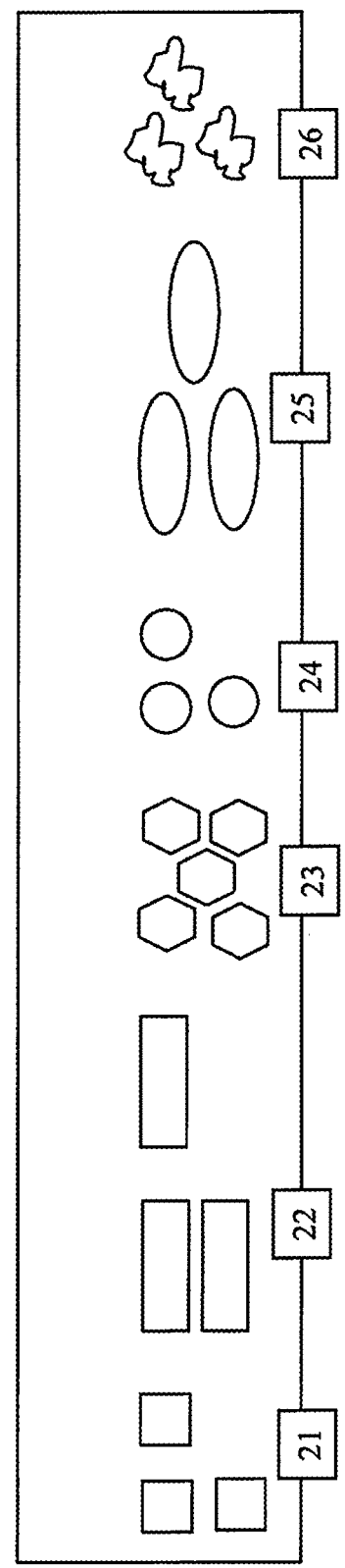
FIG. 3 depicts an illustration of possible cross-section shapes for the micropillars including square, rectangular, round, hexagonal, elliptical and non-specific.

FIG. 3 shows various Pillar cross sections including Square 21, Rectangular 22, Hexagonal 23, Round 24, Elliptical 25 and General 26. Any of these and more can be achieved using modern lithographic techniques.

On the nanometer and/or micron scale, the parameters of a textured surface might be selected to: (1) Stimulate the growth rate of cells beyond that which could be achieved on a flat surface, (2) Preferentially grow beneficial cells while hindering the growth of unwanted cells, and (3) Control the growth rate of new cells in different directions so as to match the shape of the wound bed.

Wu et al. (*Biotechnology Letters*, Vol. 33, No. 2, p.423, 2010) describes cell growth on a honeycomb structure of PLGA. In their work, osteoblast-like MG63 cells were cultured on PLGA scaffolds with greater viability as compared to the control surface. This was an important result as that surface geometry can play a role in the rate of cell growth.

Biazar et al. (*Journal of Paramedical Sciences*, Vol. 1, No. 4, 2010, p. 74) was able to pattern a polyhydroxybutyrate-co-hydroxyvalerate (PHBV) film into micro-grooves and showed that subsequent cell growth could be aligned along the preferential direction of the grooves.

Biocompatible and Biodegradable Polymers

As used herein and throughout, the term Biocompatible Polymer shall include any polymer that, when placed in direct contact with mammalian tissue, is nontoxic, non-allergenic, non-carcinogenic, non-mutagenic and/or does not cause any adverse reactions or side-effects in the adjacent tissue.

Preferably, but not necessarily, Biocompatible Polymers for use in nanopillar fabrication will include Polyvinylchloride (PVC), Polytetrafluoroethylene (PTFB), Polyethersulfone (PES), Polyethylene (PE), Polyurethane (PU), Polyetherimide (PEI), Polycarbonate (PC), Polyetheretherketone (PEEK), Polysulphone (PS), Polypropylene (PP), Polymethylmethacrylate (PMMA), Polydimethylsiloxane (PDMS), Polyhydroxybutyrate-co-hydroxyvalerate (PHBV) and/or combinations thereof.

PDMS is commercially available under the tradename of Sylgard™ and is manufactured by the Dow Corning Corporation (Midland, MI).

A particularly preferable Biocompatible and Electrically Conductive polymer is polyethylenedioxythiophene (PEDOT). Other conductive or conjugated polymers can be used including other polythiophenes and other heterocyclic polymers.

As used herein and throughout, the term Biodegradable Polymer shall include any polymer that, when placed in direct contact with living tissue slowly dissolves away with no adverse reactions or side-effects to the adjacent tissue.

In one embodiment, Biodegradable Polymers for use in nanopillar and/or micropillar fabrication will include Polylactic Acid (PLA), Polyglycolic Acid (PGA), Polyethylene glycol (PEG), Polylactic-co-glycolic acid (PLGA) and/or combinations thereof. PLGA is commercially available from Evonik Industries AG (Darmstadt, Germany).

A particularly preferable Biodegradable and UV curable Polymer is Poly glycerol-co-sebacate acrylate (PGSA). See for example, Nijst, Bruggeman, Karp, Ferreira, Zumbuehl, Bettinger and Langer, "Synthesis and Characterization of Photocurable Elastomers from Poly(glycerol-co-sebacate)", *Biomacromolecules*, Vol. 8, No. 10, p.3067, October.2007).

Superhydrophobic Surfaces and Moisture

Consider the interface between a small liquid droplet and an ideal solid flat surface on a length scale greater than 50 Å, where van der Waals and electrostatic forces play an important role. In this system, there are typically three distinct wetting regimes: (1) non-wetting with a contact angle of $\theta \approx 180$ deg (5a), (2) partial-wetting with a contact angle $0<\theta<180$, and (3) complete-wetting where $\theta \approx 0$ as shown in FIG. 5(d).

Figure 5:
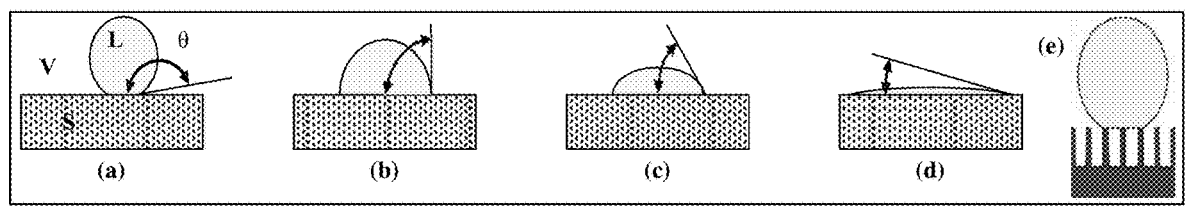
FIG. 5 depicts a droplet of water on a surface with different wetting parameters.

From energy considerations, it can be shown that the contact angle $\theta$ at the "triple-point" is defined by Young's equation such that $\gamma_{SV}-\gamma_{SL}-\gamma_{LV}*\cos\theta=0$ where $\gamma_{ij}$ (i,j=SV, SL, LV) is the surface tension (energy per unit surface area) for the Solid-Vapor, Solid-Liquid and Liquid-Vapor interfaces respectively. FIG. 5 depicts the wetting properties of a water droplet on a flat and textured surface. As the contact angle $\theta$ increases beyond 150 degrees, the surface becomes Superhydrophobic (extraordinarily water-repellent).

Aside from keeping the wound clean, Moisture Management of a wound is perhaps the most important and elusive of modern-day dressings. Some dressings will wick away moisture at too high a rate, leaving the wound overly dry. Other fabrics will not wick away enough moisture, leaving behind an attractive environment for microbes, fungi and other harmful detractors to wound healing.

Nano-engineered dressing surfaces bring an important additional parameter that can be used to optimize the rate at which moisture is being pulled away from the wound. In the present disclosure, the wettability of a nano-textured surface is controllable. By changing the size and pitch of the features patterned onto the primary dressing surface, including the perforations contained therein, we can directly control the rate at which moisture is wicked away from the wound.

Hydrophobicity is usually determined experimentally by measuring the contact angle of a water (or other liquid) droplet contacting the surface under study. The angle between the surface tangent and the water meniscus near the line of contact, measured within the droplet, gives an indication of the wettability of the surface.

For example, the water contact angle on a flat surface coated with PTFE is approximately 120 degrees. This is nominally the maximum contact angle for water on a flat (i.e. non-textured) surface. Superhydrophobic surfaces typically have a contact angle of 150 degrees or greater and require patterning of the surface to achieve these parameters.

Martines et al. (*Nano Letters*, Vol. 5, No. 10, p.2097, 2005) has shown that a forest of slender nanopillars is a highly effective water-repellent surface and that the repellency is dependent on the geometric parameters of said surface. That being said, it seems reasonable to assume that the surface patterns can be selected to achieve the optimal wetting characteristics for longer-term management of dressing moisture.

The Galvanic Cell

The galvanic cell is an electrochemical device that derives electrical energy from a chemical reaction taking place within it. Typically, a galvanic cell is comprised of two different metal electrodes immersed in an electrolyte solution. The so-called "Lemon Battery" and "Potato Battery" are examples of simple galvanic cells For a galvanic cell comprised of Silver (Ag) and Zinc (Zn) Electrodes, the Redox reaction is given by:

$$Zn_{(s)} + 2Ag^{1+}_{(aq)} \rightarrow Zn^{2+}_{(aq)} + 2Ag_{(s)}$$

where Zinc (the Anode) losses 2 electrons (Oxidation) and Silver (the Cathode) gains 2 electrons (Reduction).

Alternative electrodes could be comprised of other metals found in the so-called "electromotive series":

K, Na, Ba, Ca, Mg, Al, Mn, Zn, Cr, Cd, Fe, Ni, Sn, Pb, H, Sb, Bi, As, Cu, Hg, Ag, Pt where the more reactive elements are to the left and the less reactive elements are to the right.

Applying these concepts to the disclosed Nano-Enhanced Wound dressing system, electrons will travel from the Silver-containing micropillars to the Zinc-containing micropillars through the primary dressing surface upon which they sit. And, ions (charged atoms) will be pushed (via electromotive force or EMF) into the wound electrolyte and subsequently the wound bed. In this way, there can be many more ions in the wound electrolyte than there otherwise would be without galvanic action. And this causes a significant enhancement in anti-microbial action.

An important parameter for any galvanic cell (among other things) is the surface area between the electrolyte and the two electrodes immersed therein. When this surface area is increased, the amount of current available increases and the current capacity (in uA-hrs) is also increased. This is important in the context of a silver-containing dressing because the greater the surface area of contact, the more silver ions will be "pushed" into the wound, with quicker healing resulting. In the disclosed embodiments, the numerous Polymer Protuberances that extend into the wound provide a far greater amount of surface area as compared to a flat surface, which forms the basis and mechanism for increased response.

When activated by saline solution (sodium chloride in water) and placed against the wound, the nano-enhanced dressing will exhibit galvanic action to produce an electric voltage (and current) that is supplemental and supportive of the natural electrochemical reaction of the human skin in the presence of a wound, thereby facilitating the healing process.

Figure 10:
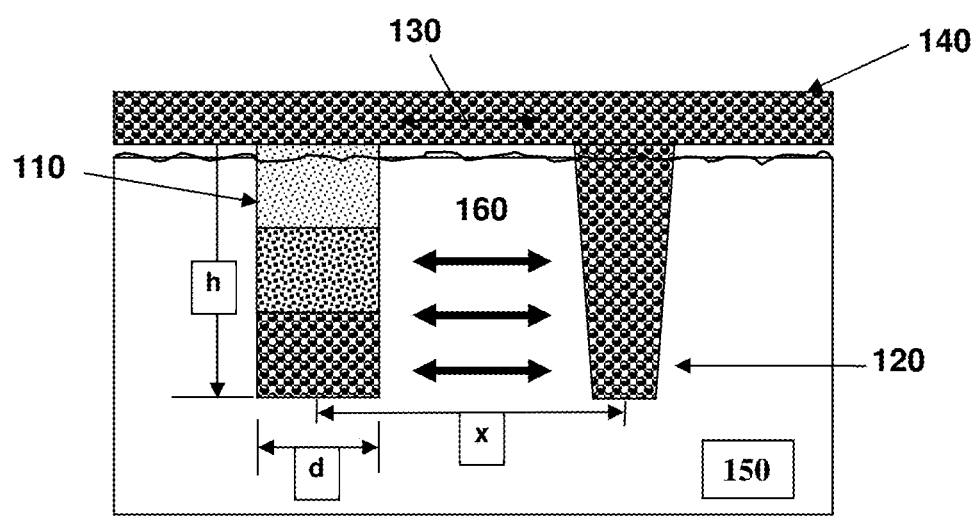
FIG. 10 depicts an embodiment for two micropillars (out of many micropillars on the primary dressing surface) that "communicate" electrically with each other thereby forming a galvanic cell.

FIG. 10 shows a schematic representation of how this three-dimensional process can work. In particular, a Galvanic Cell comprised of two nano-particle containing micropillars are at least partly inserted into a wound electrolyte wherein the micropillars are mounted onto a conductive Primary Dressing Surface (140) that also has metallic nanoparticles embedded therein (to make it conductive). Preferably, but not necessarily, the micropillars contain nanoparticles of silver and zinc. In this specific embodiment, the micropillars are comprised of multiple layers (110). In this embodiment, three layers are shown but it could be many and each layer has a different volume fraction of nanoparticles within. The micropillars can be tapered in one embodiment. As the pillar dissolves away over time, the first layer releases the nanoparticles contained therein. By changing the amount of nanoparticles used in each layer, the release rate during the lifetime of the bandage can change. For example, more nanoparticles can be located in the deepest layer and fewer in the shallowest layer (or vice versa). And these layers can each have a different molecular weight, causing them to dissolve at different rates.

The micropillars can also contain a uniform distribution of nano-particles (120). In addition, the shape of the micropillars can change, which will also affect the rate of dissolving. The narrow tip of a cone will dissolve more quickly than a thick base. (120) As a result, the three-dimensional method is extremely flexible in that the micropillar shape, molecular weight (of the polymer), volume of nanoparticles mixed into the polymer and layering all help to achieve the varying and beneficial release rate of medicinals.

With reference to FIG. 10, it is shown that d is the diameter of the micropillar, "h" is the height of the micropillar and "x" is the center-to-center distance from one micropillar (110) to a neighboring micropillar (120).

Electrons flow between the micropillars in the conductive Primary Dressing surface (to close the circuit) (130) and ions (160) flow between the micropillars inserted into the wound electrolyte to yield a 3D current distribution inside the wound, and not just a surface effect as with prior art wound dressings. In particular, ions will flow from the surface-revealed nanoparticles into and out of the wound electrolyte (150) at various depths while electrons will flow in the conductive surface of the primary dressing, to complete a single micro galvanic cell. And, there are many thousands to many millions of such micro galvanic cells integrated across the primary dressing surface that interact with the wound bed. In any single micro galvanic cell, the current that flows is a function (by Ohms Law) of the electrochemical potential developed across the two micropillars (by virtue of the surface-revealed metallic nanoparticles contained therein) and the resistance to electron flow in the primary dressing surface, which we control by the volume (or weight) fraction of conductive nanoparticles contained in/on the polymer used to fashion the primary dressing surface (which may, or may not, be the same polymers that are used to fashion the micropillars) and the distance x between the micropillars. Also of significant importance to the functioning of a micro galvanic cell is the surface area of the micropillars in contact with the wound electrolyte ($\pi dh$). A larger surface area means there are more surface-revealed nanoparticles taking part in the galvanic process, thereby increasing the current capacity in uA-hrs. Since the polymer comprising the micropillars is dissolving (i.e. d is getting smaller in time due to biodegradation), as time passes, more and more of the nanoparticles contained therein are surface-revealed, thereby allowing them to participate in the galvanic process.

EMBODIMENTS OF THE DISCLOSURE

In an embodiment according to the present disclosure, a dermal drug delivery platform is deployed as part of an advanced Adhesive Bandage system as illustrated in FIG. 1. In this example, an Adhesive Bandage System 1 is comprised of a Nano-Enhanced Wound Dressing 2 that is further comprised of a Primary Dressing 3 and a Secondary Dressing 4 held in abeyance against the wound bed 5 using Adhesive Strips (aka Adhesive Tabs) 6 on opposite sides of said Primary Dressing 3.

It is shown in FIG. 1 that on the wound-facing side of Primary Dressing 3 there is an arrangement of Polymer Islands 7 formed thereupon. These Polymer Islands 7 are spaced apart on the Primary Dressing 3, so as to allow the dressing to remain conformable/pliable and to facilitate the flow of exudate through the dressing system as needed.

In one embodiment, the Primary Dressing 3 is a woven fabric and the Polymer Islands 7 are Hot Embossed into the woven surface.

The Polymer Islands 7 may be round, square, rectangular, elliptical or hexagonal in shape and they would be spaced across the Primary Dressing 3 in an array, covering a substantial portion of the area.

In one embodiment, the Polymer Islands 7 would be fashioned from a conductive, biocompatible polymer.

It should be noted that regarding Polymer Island 7, there is an arrangement of nano and/or micro scale Polymer Protuberances 8a, 8b, 8c and/or 8d formed thereupon wherein each polymer protuberance is further comprised of nanoparticles embedded within the polymer. In this particular example, Polymer Protuberances 8a, 8b and 8c are embedded with Nanoparticles 9a, 9b and 9c respectively. Or, as in the case of 8d, there could be several different layers of nanoparticles that comprise a single polymer protuberance. In either case, Nanoparticles 9a, 9b and 9c comprise equivalently a selection of Medicinal Species 9a, 9b and 9c respectively, that are contained within the Polymer Protuberances.

In an embodiment, the Nanoparticles (also known as "Medicinal Species") would be selected from the following metallic species: Silver (Ag), Gold (Au), Copper (Cu), Platinum (Pt), Palladium (Pd), Zinc (Zn) and/or combinations thereof.

Other materials to be incorporated into (or onto) the Polymer Protuberances as medicinal species might include: Amitriptyline, Amantadine, Baclofen, Bupivacaine, Clonidine, Cyclobenzaprine, Diclofenac, Gabapentin, Ketamine, Ketoprofen, Lidocaine, Menthol, Mexiletine, Morphine, Nifedipine, Orphenadrine, Phenytoin, Prilocaine, Tramadol, Verapamil, and growth factors including but not limited to, Interleukins (IL-6, IL-7, IL-8), Keratinocyte growth factor (KGF), Hepatocyte growth factor (HGF), and/or combinations thereof.

In one embodiment, the Nanoparticles may be spherical in shape with a diameter ranging from 2 nm to 500 nm.

In one embodiment, the Polymer Protuberances would take the form of Pillars, and the Pillars would have a cross sectional shape that is square, round, elliptical, rectangular or general.

In one embodiment, the diameter (in the case of round pillars) or width (in the case of square pillars) ranging from 1 µm to 1000 µm.

In one embodiment, the height of the Polymer Protuberances range from 1 µm and 500 µm so as to readily engage the wound bed.

In one embodiment, each Polymer Island 7 may comprise numerous (and therefore smaller) Polymer Protuberances 8a, 8b, 8c and/or 8d formed thereupon, with any number of Medicinal Species 9a, 9b and 9c infused therein as nanoparticles.

In one embodiment, Polymer Island 7 and/or Primary Dressing 3 may further comprise numerous perforations that would aid in moisture management.

In one embodiment, Primary Dressing 3 may comprise a material that is flexible and allows wound exudate to readily pass through it.

In one embodiment, Secondary Dressing 4 may comprise a material that is a reservoir for moisture and allows for additional moisture management of the dressing system as a whole.

Also disclosed herein are the various methods of fabricating the dermal drug delivery platform used for the Nano-Enhanced Wound dressings. Adhesive Bandages must be fabricated in high volume, they must be inexpensive and widely available.

One method of making the dermal drug delivery platform comprises dispersing medicinal nanoparticles in at least one biocompatible and/or biodegradable polymer; and depositing the medicinal nanoparticle containing polymer onto a primary dressing surface to form three-dimensional polymer protuberance.

This method may further comprise placing one or more secondary layers over the primary dressing surface on the side opposite the three-dimensional polymer protuberance, as well as placing an outer layer on top of the secondary layers, such that the secondary layers are located between the primary dressing and the outer layer.

Figure 6:
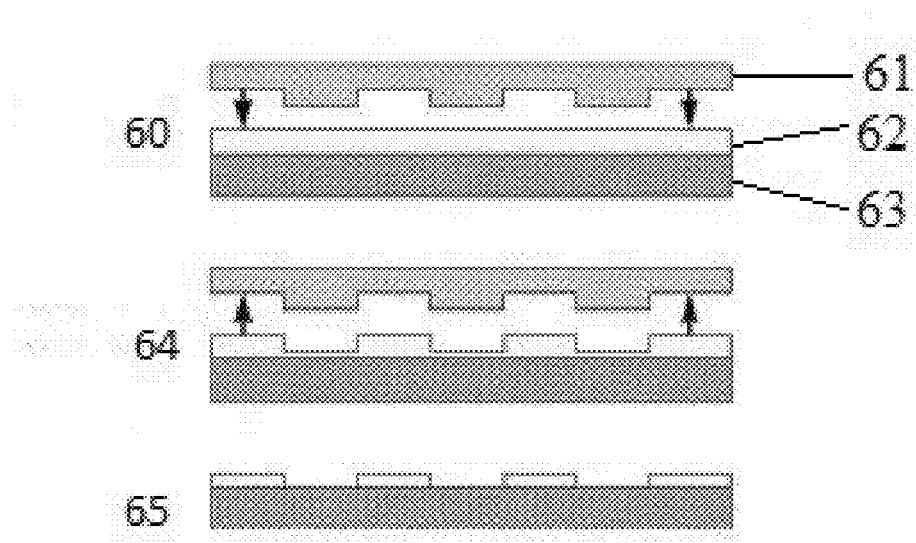
FIG. 6 depicts several important steps in the process of nano-imprint lithography (NIL), one possible method of fabricating the nano-enhanced wound dressing.

Among the several different candidate methods of fabrication, Nanoimprint Lithography (NIL), might play an important role. A schematic representation of this is shown in FIG. 6, and is described in Nanoimprint Lithography (see Chou et al. (*Applied Physics Letters*, Vol. 67, p.3114, 1995)). The method involves the use of a hard mold with nanoscale and/or microscale surface-relief features thereon (61) that is pressed against a polymer material (62) previously deposited onto a substrate (63). Under the correct conditions of temperature, pressure and/or UV illumination, takes the shape of the mold surface (64), with unwanted polymer being removed from the substrate through an etching step, such as reactive ion etching, that exposes the substrate. (65)

Nanoimprint Lithography is particularly attractive because of its inherently high-throughput and low-cost. Using NIL, large macroscopic regions with nanometer-sized features can be "printed" at the same time. The printed area is only dependent on the size of the mold master.

Figure 7:
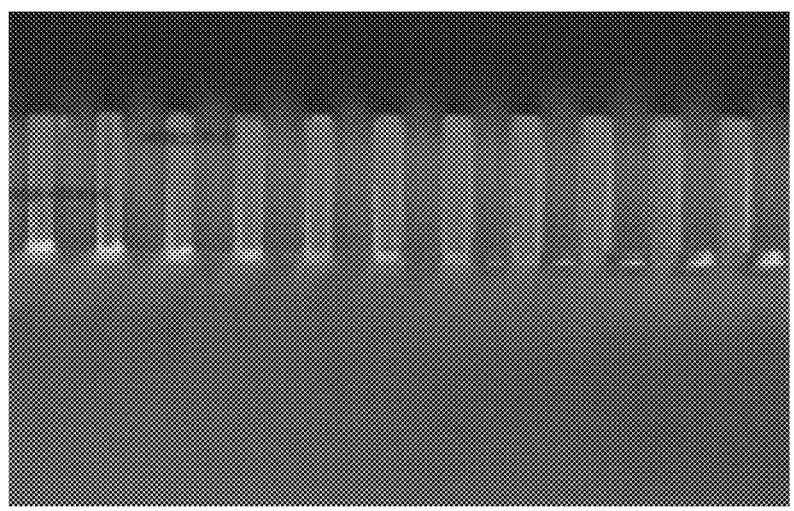
FIG. 7 depicts a DIC microscope image of micropillars fashioned from silicon that can be used as a master mold.

In one method of fabrication, a master mold is fashioned from a Silicon Wafer using traditional lithographic methods including Contact, Optical and/or Electron Beam (aka Ebeam) Lithography. Contact Lithography is used for surface features on the order of tens of microns down to 1 µm (nominally), Optical Lithography is used for surface features on the order of 1 micron down to 200 nm (nominally) and Ebeam Lithography is used for surface features on the order of 200 nm down to 10 nm (nominally). When making the master mold, resist is spun onto a silicon wafer surface and exposed through a mask so that certain features are exposed with ultra-violet (UV) light and others are not (depending on the openings in the mask). Those features in the (positive) resist that are exposed with UV light will dissolve readily in developer solution. Those regions in the (positive) resist that are unexposed will remain after development. Once the pattern in the mask is transferred into the resist layer on the silicon wafer (i.e. there are "patterned openings" in the resist layer that correspond to the patterned openings in the mask), we use Reactive Ion Etching (RIE) or Deep Reactive Ion Etching (DRIE) methods to etch the pattern into the surface of the silicon wafer (the master mold surface, see FIG. 7). After the etching of the silicon is completed, any remaining resist is removed using wet solvent and/or Oxygen Plasma cleaning methods. At this time, the master mold has a pattern on it that is complementary to the pattern of interest. For example, if the Polymer Protuberances are to be tapered cones, as shown in FIG. 1, the master mold would have tapered pits on the surface.

Prior to using the master mold, a non-stick (aka release) agent (such as Teflon or Perfluorooctytrichlorosilane (FOTS)) is deposited onto its surface, so that the imprinted polymer doesn't stick to the mold surface. The mold will presumably be used many times over and we need to keep it free of residue buildup.

In one embodiment, the master mold would be used to make numerous secondary molds and only the secondary molds would be used in the imprinting process thereby extending the life of the master mold indefinitely.

After the master mold is completed (with whatever nano and or micro-textured surface features fabricated thereon), medicinal species 1 nanoparticles are mixed into a solvent along with polymer granules and magnetically stirred to form a species 1, semi-viscous polymer liquid. This procedure can be continued with species 2, semi-viscous polymer liquid, etc.

In one embodiment, the polymer granules may be comprised of PLGA.

In one embodiment, the medicinal species 1 nanoparticles will be comprised of silver, and the medicinal species 2 nanoparticles will be comprised of zinc.

In one embodiment, the solvent is comprised of: acetone, toluene, methanol, ethanol, isopropyl alcohol (IPA), nmethylpyrrolidone (NMP), propylene glycol (PG), propylene glycol methyl ethyl acetate (PGMEA) or combinations thereof.

Silver nanoparticles are available from NanoComposix (San Diego, CA) or Ted Pella Inc (Redding, CA).

Gold nanoparticles with diameters of: 5, 7, 10, 12, 15, 17, 20, 30, 40, 40, 60, 70, 80, 90 and 100 nm are available from Ted Pella Inc (Redding, CA). Gold nanoparticles as small as 2 nm are available from BBI Solutions (Cardiff, UK).

Zinc nanoparticles in the form of a gray powder with diameters between 30-60 nm and 60-80 nm are available from Nanoshel (Wilmington, DE). Other metal nanoparticles available from Nanoshel include: Silver, Aluminum, Gold, Platinum, Titanium, Boron and several alloys such as Cu/Zn, Ni/Ti and Fe/Ni to name a few.

Silicon wafers are then prepared by first depositing and/or growing a Release Layer thereupon. The Release Layer might be comprised of: Thermal Oxide, LPCVD Oxide, PECVD Oxide, Sputtered Oxide, Evaporated Oxide, LPCVD Poly Silicon, PECVD Amorphous Silicon, or any one of a number of different metals (Aluminum, Gold, Chrome, Titanium, etc), or any one of a number of different polymers (Resist, Omnicoat, etc).

Following this, the specie 1 laden liquid polymer is spun, sprayed or otherwise deposited over-top of the Release Layer.

Following this, the specie 2 laden liquid polymer is spun, sprayed or otherwise deposited over the specie 1 laden liquid polymer, etc. In this way, there are multiple layers of different medicinal species, one over top of the next.

Preferably, but not necessarily, the polymer deposition method of choice will be: Spin Coating, Spray Coating, Silk-Screen Printing, Ink-Jet Printing, Slot-Die Coating, Gravure Printing, Flexo Printing and/or combinations of the above.

Spin Coaters, such as the Cee 200X, are available from Brewer Science Inc. (Rolla, MO) to spin a nanoparticle-infused liquid polymer layer onto a surface.

Spray Coaters, such as the AltaSpray Module in the Suss Gamma Custer (Suss MicroTec AG, Garching, Germany), can be used to coat virtually any surface with a nanoparticle-infused liquid polymer layer onto a surface.

Following this, the master mold is pressed against the silicon wafer under controlled conditions of pressure and temperature wherein the multiple layers will reflow (i.e. fill-in all the little nooks and crannies on the mold surface).

After heating, pressing and/or uv-curing, the master mold is pulled away from the Silicon Wafer with the desired surface (an array of polymer protuberances) embossed into the multiple polymer layers.

Following this, a Release Agent (Buffered Oxide Etch (BOE) or Vapor HF in the case of an Oxide Release Layer, KOH or XeF2 RIE in the case of a Silicon Release Layer, or any number of different metal etchants (Aluminum Etch, Gold Etch, etc) in the case of a Metal Release Layer or solvents (Acetone, Toluene, PGMEA, etc) in the case of a Polymer Release Layer)) is used to Lift-Off the freshly-molded multiple-specie polymer protuberance layer. After Lift-Off and Harvesting of the multiple-specie polymer protuberance layer, it can be applied to the dressing surface (thereby converting a conventional dressing surface into a nano-enhanced dressing surface) and/or any other surface that requires anti-microbial action.

An alternative to Lift-Off, Harvesting and Application of the multiple-specie, polymer protuberance layer is to hot emboss the polymer protuberances directly onto the dressing fabric surface. In this scenario, the specie-laden polymer is spun, sprayed or otherwise deposited onto the dressing fabric and a mold is pressed against the polymer/fabric under the correct conditions of temperature and pressure until the polymer reflows both into the dressing fabric and the nooks and crannies of the mold surface.

In yet another preferred method of fabrication, a Pillar Array is UV Imprinted onto the Primary Dressing Surface (see for example, Shinohara, Goto, Kasahara and Mizuno, "Fabrication of a Polymer High-Aspect-Ratio Pillar Array using UV Imprinting, Micromachines, Vol. 4, p.157, 2013). In this method, a biocompatible polymer is silk screened onto the Primary Dressing Surface to form a pattern of millimeter-sized Polymer Islands. Following this, the Primary Dressing Surface would be compressed against a flat heated surface in such a manner so that the Polymer Islands would locally fuse the textile threads beneath them, and in so doing, each Polymer Island would exhibit a flat surface on which the Polymer Protuberances will be subsequently formed. In-between the fused Polymer Islands would be conventional dressing materials that allow the overall dressing to remain conformable on a macroscopic scale.

Preferably, but not necessarily, the biocompatible polymer is conductive.

In one embodiment, the biocompatible polymer is PEDOT or PLGA containing metallic nanoparticles.

After forming the flat islands (i.e. the substrates) across the primary dressing surface, medicinal species 1 laden polymer is spray-coated or otherwise deposited onto the Primary Dressing Surface. Following that, mask/mold cavity 1 is placed against the freshly deposited polymer and UV illumination is used to cure the polymer through the mask/mold cavity thereby cross-linking only those open regions in the mask/mold cavity. In those regions that did not see any UV light, the polymer has not been cross-linked and is easily removed in a subsequent developer and/or solvent rinse. A pattern of medicinal species 1 infused Polymer Protuberances (those that correspond to the openings in mask/mold cavity 1) are fabricated in this way.

In an identical manner, medicinal specie 2 laden polymer is fashioned into a different pattern of medicinal species 2 infused Polymer Protuberances (those that correspond to the openings in mask/mold cavity 2) and likewise for species 3,4, 5 and mask/mold cavities 3,4,5 respectively. In this way, the Primary Dressing Surface can be comprised of numerous and different medicinal specie infused Polymer Protuberances.

In one embodiment, the medicinal species laden polymer is PGSA and the species is silver nanoparticles.

In one embodiment, the medicinal species laden polymer is PGSA and the species is zinc nanoparticles.

In one embodiment, the mask/mold cavities are comprised of a quartz (i.e. uv-transparent) mask with a relief structure etched into the surface and a thin chrome layer everywhere the quartz has not been etched. The chrome layer would have openings in it to allow the passage of uv light. In those regions where the chrome layer blocks the uv light from passing through, the PGSA remains uncured and easily removed. After exposure, we soak the dressing fabric in developer and/or solvent which dissolves away only those regions of PGSA that have not been exposed. The regions that have been exposed (i.e. cross-linked) become insoluble in the developer solution and remain on the Primary Dressing Surface as an array of Polymer Protuberances.

In one embodiment, the Polymer Protuberances would be circular in cross section with a tapered conical shape.

In still yet another preferred method of fabrication Reactive Ion Etching (RIE) methods are used to pattern the polymer layers that have been deposited onto the Primary Dressing Surface. By way of example, PLGA1 polymer is formed by mixing medicinal species 1 nanoparticles and PLGA into a solvent and magnetically stirring. And likewise, PLGA2 polymer is formed by mixing medicinal specie 2 nanoparticles and PLGA into a solvent and magnetically stirring, etc.

Following this, PLGA1, PLGA2, PLGA3 layers of medicinal specie infused polymer layers are sprayed or otherwise deposited onto the Primary Dressing Surface (there could be more than 3). In this example, the Primary Dressing Surface is already flat and receptive to micro/nano fabrication. After Soft baking (to drive out the solvents and form a solid multi-layer stack), an Aluminum hard mask layer is sputter-deposited across polymer stack.

Following this, a layer of photoresist is spun-coated, sprayed-on or otherwise deposited onto the Aluminum layer and soft baked.

Following this, the photoresist is patterned using a mask and Contact Aligner and/or Stepper Lithography Tool. After exposure, the photoresist is developed and only those regions that were exposed are developed away (in the case of positive-tone photoresist). After development, a wet Aluminum Etchant is used to remove the Aluminum hardmask only in those regions were the positive-tone photoresist was exposed thereby transferring the pattern in the mask to the Aluminum layer.

After Aluminum Etch, CF4 and/or O2 Reactive Ion Etch (RIE) is used to etch down through the medicinal species containing polymer layers (using the Aluminum as a masking layer). When the RIE is completed, the remaining Aluminum mask is etched away and the pattern of Polymer Protuberances remain.

Medical Dressings include gauze, films, gels, foams, hydrocolloids, alginates, hydrogels, polysaccharide pastes granules and beads, among other things.

Occlusive dressings are made from substances that are impervious to moisture such as plastic or latex.

Hydrocolloid Dressings are typically biodegradable, non-breathable and adheres to the skin without any additional adhesion mechanism (tape or other). Typically, hydrocolloid dressings have an active dressing surface comprised of a cross-linked adhesive containing gelatin, pectin, carboxy-methylcellulose and any number of other polymers that absorb water and swell, thereby forming a moist, soft, gel over the wound surface that promotes healing.

Of significant importance to the galvanic action of "pushing" metallic ions into the wound bed via electrochemical forces (and achieving the anti-microbial response produced thereby) is the need for an electrically conductive electrolyte medium. This electrolyte is typically found within the wound exudate itself. However, wound exudate can sometimes dry up, thereby reducing the galvanic action considerably. When this happens, it may be necessary to periodically refresh the wound exudate by applying a saline rinse. The adhesive tabs on the Nano-Enhanced Wound Dressing are engineered to allow a fresh stream of saline solution to pass between the wound bed and the primary dressing surface, thereby reinvigorating the galvanic action.

In one embodiment, the medicinal species would be incorporated into the Polymer Protuberances as entombed nanoparticles that are released when the protuberances dissolve away. However, sometimes the medicinal species might be in the form of a coating that is deposited overtop of the Polymer Protuberances.

In one possible embodiment, the Polymer Protuberances are coated or otherwise containing a wax (paraffin) like substance that only allows the release of entombed medicinals in response to the human body temperature (98.6 degrees Fahrenheit).

In another possible embodiment, the Polymer Protuberances are activated (i.e. they release their medicinal constituents) as a result of some stimulus. For example, there could be: activation by a saline rinse, activation by sweat or perspiration, activation by body temperature, activation by wound exudate and/or activation by magnetic or electric means.

Depending on the use and type of wound to be treated, the medicinal nanoparticles may be uniformly distributed within the polymer protuberances. In an alternative embodiment, the medicinal nanoparticles may be non-uniformly distributed within the polymer protuberances so as to facilitate a non-uniform release of anti-microbial and/or anti-biotic agents.

The speed with which the nanoparticles are released into the wound is a function of the polymer protuberances, including the material itself, the concentration of nanoparticles contained therein, the size of the protuberances, and shape of the protuberances. For example, higher molecular weight polymers dissolve more slowly than lower molecular weight polymers. Therefore, a wound healing system intended to treat a wound slowly over a long period of time may comprise a higher molecular weight polymer than a wound healing system intended to treat a wound over a shorter period of time.

In certain embodiments, it is desirable to release multiple medicines at different times with different rates to from an optimal wound treatment system. In this case, a medicine that is desirably introduced first into a wound, such as pain killer, can be contained in a low molecular weight polymer. Subsequent medicines that are to be introduced into a wound in a desired order can then be contained in increasingly higher molecular weight polymers. In this way, a single wound healing system provides the ability to tune the release rate of medicinal nanoparticles very specifically.

In addition, the size and shape of the polymer protuberances will affect the release characteristics of the nanoparticles contained therein. For instance, larger diameter protuberances will take longer to controllably release their entombed dose of nanoparticles (aka nanomedicinals) than smaller diameter protuberances. And, if the protuberances should take on the shape of a tapered cone, the smaller end will dissolve more quickly than the larger base.

With regard to a non-uniform distribution of nanoparticles in the polymer protuberances, such an embodiment provides much flexibility in the release rate of nanomedicinals into the wound. For example, micropillars can be comprised of many separate layers of PGSA, with each having a different volume (or weight) fraction of nanoparticles. By making micropillars that have such a gradient of nanoparticles from the tip to the base, one can alter the release rate of nanomedicinals into the wound. In one embodiment, a greater concentration of medicinal nanoparticles can be initially introduced into a wound, and taper off the amount over time by forming micropillars with more nanoparticles in the tip and less in the base. The opposite is also true, e.g., ramp up the amount of medicine that is introduce into a wound via nanoparticles by forming micropillars with less nanoparticles in the tip and more in the base.

Preferably, but not necessarily, materials to be used for the adhesive strip include vinyl, latex and/or combinations thereof.

In one embodiment according to the present disclosure, numerous PGSA micropillars with nanoparticles contained therein are photolithographically fashioned onto a conductive, perforated PLGA primary Dressing surface. This is represented in FIGS. 8A-8R, which are described in more detail below.

Figure 8A:
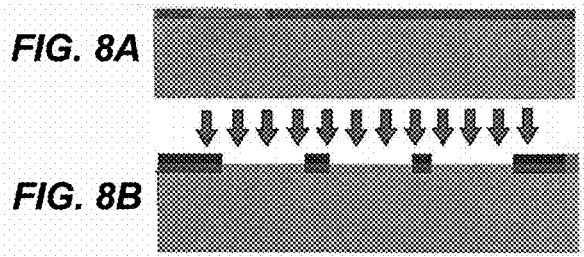
FIGS. 8A-8R depict various steps in one embodiment for a process for making a nano-enhanced wound dressing system according to an embodiment.

Starting with a 100 mm diameter, 525 µm thick, Single-Side Polished (SSP), 1-0-0 crystalline Silicon wafer, a layer of Photoresist is spin coated on the top surface, as shown in FIG. 8A.

Mask 1 is positioned against the photoresist and exposed with ultraviolet (UV) light using a Contact Aligner, as shown in FIG. 8B. Because the resist is positive tone, exposure to UV light causes scission of the long chain polymer molecules in the resist thereby making it more soluble in developer solution (as compared to those regions that are not exposed). Openings (i.e. transparent regions) in Mask1 allow UV light to pass through the mask to illuminate the resist beneath. Opaque regions of the mask (shown in black, in FIG. 8B) do not allow light to pass.

After (through the mask) exposure and development, the resist is cleared out in those regions where it had been exposed, as shown in FIG. 8C. And, in those regions where it had not been exposed, the resist remains on the surface of the Silicon Wafer. Processing of the resist in this way (the so-called lithographic process) allows the pattern in Mask1 (the Primary Dressing dimensions and geometry) to transfer into the resist layer.

Figure 8D:

FIG. 8D illustrates the Silicon Wafer after Deep Reactive Ion Etching (DRIE) using an SF6/C4F8 Bosch Etch Process to a nominal depth of 100 µm into the surface.

Figure 8E:

FIG. 8E shows the same cross section as FIG. 8D, except the remaining resist mask has been removed using an oxygen (O2) plasma treatment and/or hot solvent bath. FIG. 8E illustrates the Mold Cavity for the Primary Dressing. The Lateral Extent of the Primary Dressing is determined by the geometric details in Mask1. The Thickness of the Primary Dressing is determined by the DRIE etch depth. In one embodiment, the Primary Dressing will have dimensions of 20 mm×15 mm×100 µm thick.

In FIG. 8F, a conformal, Sacrificial Release Layer (500 nm of Copper or Other) has been blanket deposited across the wafer. This Sacrificial Release Layer coats the bottom, sidewalls and top of the wafer and allows for the Primary Dressing to be Lifted Off at a later step.

Figure 8G:

In FIG. 8G, the mold cavity is coarsely filled with Polymer 1, which comprises a viscous mixture of suspended nanoparticles and dissolved polymer granules in a solvent. In one embodiment, Silver Nanoparticles (5 nm-10 nm-20 nm diameter) will be suspended in a viscous mixture of PLGA (Poly-lactic-co-glycolic acid) granules dissolved in solvent. The viscous liquid will be poured, troweled or otherwise deposited into the Mold Cavity.

Figure 8H:

In FIG. 8H, a separately-prepared PDMS pad is pressed against the nanoparticle-laden PLGA under appropriate conditions of Pressure and Temperature to cause the PLGA/Nanoparticle mixture to reflow and fill all of the little nooks and crannies of the Mold Cavity. The Mold Cavity for the Primary Dressing has many hundreds (or thousands) of Silicon "Posts" that the PLGA/Nanoparticles must flow around once the volume of the Mold Cavity is completely filled. In FIG. 8H, there are only two Silicon Posts shown and they are each conformally coated with the Sacrificial Release Layer. These Posts correspond to opaque regions in the original Mask1. When the Primary Dressing is released from the Mold Cavity, in the location of the each and every Silicon Post will be a through hole within which wound effluent can pass. The number, size, shape and spacing of the numerous Silicon Posts in the Mold Cavity will help to determine how fast liquids can pass through the Primary Dressing. They will also help to determine the wettability of the Primary Dressing surface.

Figure 8I:

FIG. 8I shows the nanoparticle-laden PLGA over-filling the Mold Cavity after removal of the PDMS pad.

Figure 8J:
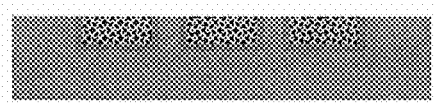

In FIG. 8J, Chemical Mechanical Polishing (CMP) is used to "planarize" the surface of the wafer (i.e. remove any portions of polymer that stick out, above the surface of the wafer). Ideally, a flat surface is available to work with in the subsequent processing steps.

Figure 8K:
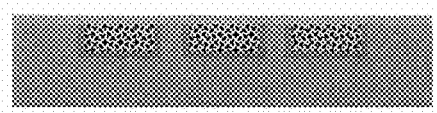

In FIG. 8K, the wafer is coated with a nanoparticle-laden, UV-curable Polymer 2. In one embodiment, Silver (Zinc, Gold or Other) nanoparticles will be mixed with PGSA (Poly-glycerol-co-sebacate) polymer to form a viscous, nanoparticle-laden liquid that is spun on or sprayed across the wafer.

Figure 8L:
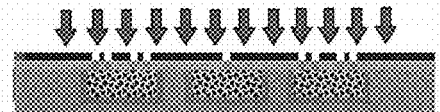

In FIG. 8L, Mask 2 is placed against the baked Polymer 2 film and exposed with UV light. Polymer 2 (nanoparticle-laden PGSA) is UV curable so that ultraviolet light causes the polymer to cross-link thereby reducing its solubility in developer.

Figure 8M:
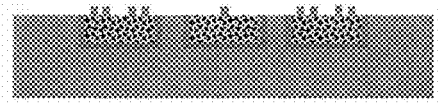

After development, only those regions of Polymer 2 that have been exposed with UV light remain, as shown in FIG. 8M. FIG. 8M shows an array of Polymer2 micropillars affixed to the top surface of the Primary Dressing. Tentative dimensions for the micropillars will be 5 µm diameter and 10 µm tall.

Figure 8N:
Figure 8O:
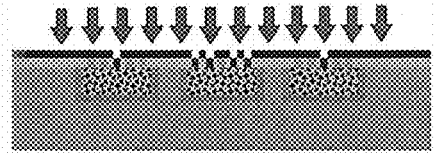
Figure 8P:
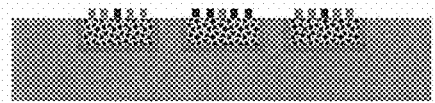

In Figures FIG. 8N-8P, the same set of steps as in FIG. 8K-8M are performed. FIG. 8N shows a new nanoparticle-laden Polymer 3 deposited across the wafer. Polymer 2 and Polymer 3 may or may not be the same base polymers, but they will have different nanoparticles contained therein. Polymer 3 is spun on or sprayed on and more or less disregards the existing set of Polymer 2 micropillars.

After deposition of Polymer 3, Mask 3 is placed in contact with it and UV illumination causes the polymer to cross-link in those areas of the mask that are open as shown in FIG. 8O. The openings in Mask 2 are different from the openings in Mask 3.

After development, in FIG. 8P, Polymer 2 and Polymer 3 micropillars remain across the surface of the Primary Dressing. Repeating this process (Deposit Nanoparticle-Laden Polymer, Expose, Develop Away Non-Exposed Regions, etc) any number of times would allow numerous micropillars to be fashioned across the surface of the Primary Dressing.

After processing the micropillars, the Primary Dressing must be released from the Silicon Wafer. Throughout this whole process, the Silicon Wafer has been a temporary "positioning vehicle" for holding the Primary Dressing Surface and positioning the micropillars relative to each other. The Alignment Marks required for mask registration were etched into the Silicon wafer at the onset. Otherwise, it would be impossible to precisely position one family of micropillars relative to another. This gives considerable positional freedom of micropillar ensemble 1 versus micropillar ensemble 2 versus micropillar ensemble N.

Figure 8Q:
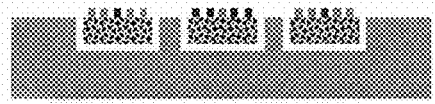
Figure 8R:

And, part of the development process will include changes in geometry, size, shape, spacing, etc of these micropillars which is only possible because there is a stable "platform" (i.e. the Silicon Wafer) from which to work. In the end, the whole wafer is immersed in Copper Etchant and the Sacrificial Release Layer is eaten away as shown in FIG. 8Q.

Once the Sacrificial Release Layer is etched away, there is no inherent adhesion between the Primary Dressing (with all of its micropillars) and the underlying Silicon Wafer so the dressing lifts off. Once harvested from the sacrificial etchant and rinsed in DI Water, the Primary Dressing is readied for subsequent attachment to the Secondary Dressing, as shown in FIG. 8R.

After attachment to the Secondary Dressing, a water impermeable Adhesive Strip is fashioned to hold the Primary/Secondary Dressing against the wound area in the same manner as a conventional Band-Aid.

In one embodiment, the Secondary Dressing is woven from a material that may include: cotton, wool, polyester, nylon, rayon, silk and/or combinations of same.

In one embodiment, the size (diameter, height) and spacing (aka pitch) of the micropillars, including the geometrical pattern that they make when integrated onto the Primary Dressing surface is chosen so as to generate an electrochemical (i.e., galvanic) charge that is comparable to or greater than the natural charge produced by the skin during healing in the absence of the dressing.

Figure 9A:
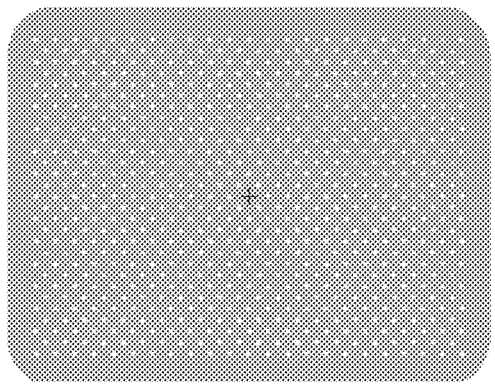
FIG. 9A depicts a perforated primary dressing surface according to an embodiment.
Figure 9B:
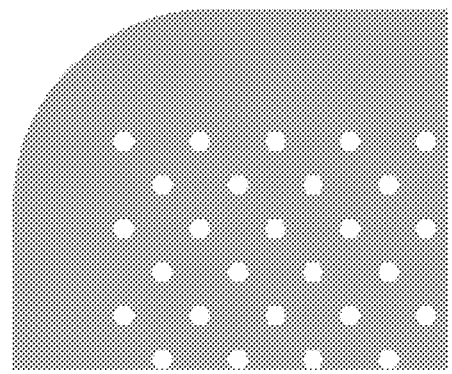
FIG. 9B depicts a close-up view of the same perforated primary dressing surface of FIG. 9A.

FIGS. 9A-9F show various patterns and arrays of perforations and pillars that can be used according to different embodiments. For example, FIG. 9A shows a Primary Dressing Surface with FIG. 9B showing a close-up (without micropillars) of hexagonal, circular or other perforations used for moisture management and compliance).

Figure 9C:
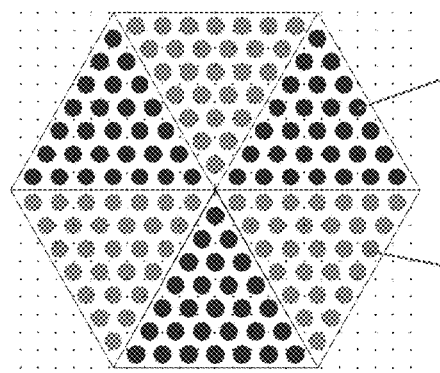
FIG. 9C depicts two types of micropillars arranged into an iso(sceles)-hexagonal geometry.
Figure 9D:
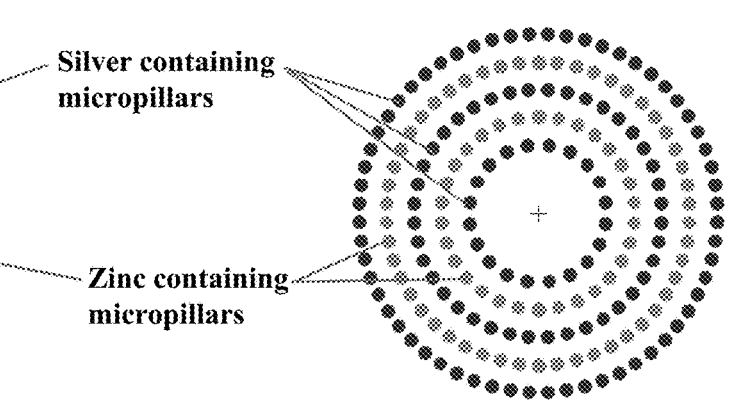
FIG. 9D depicts two types of micropillars arranged into a concentric circular geometry.

FIG. 9C shows iso(sceles)-hexagonal arrays of micropillars, while FIG. 9D depicts concentric circular arrays of 10 µm diameter micropillars. In this figure, black micropillars represent silver nano-particles, and grey micropillars represent zinc nano-particles.

Figure 9E:
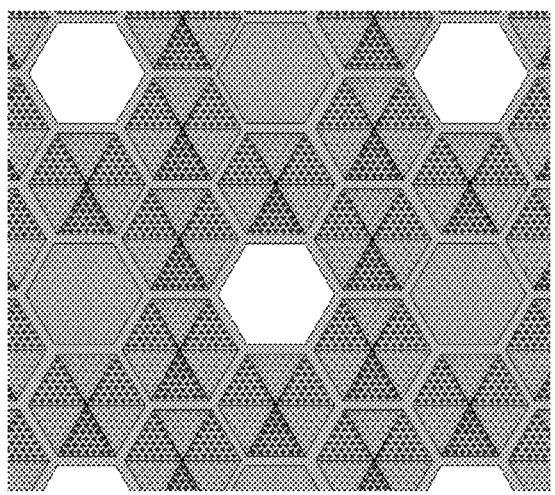
FIG. 9E depicts a close-up view of a primary dressing surface with hexagonal perforations and 3 types of micropillars contained thereon and arranged into an iso-hexagonal geometry.
Figure 9F:
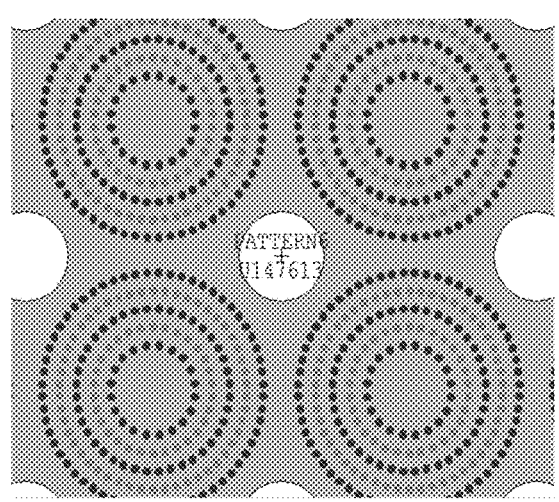
FIG. 9F depicts an embodiment for a close-up view of a primary dressing surface with circular perforations and 2 types of micropillars contained thereon and arranged into a concentric circular geometry.

Multiple instances of the iso-hexagonal micropillars on the Primary Dressing Surface are shown in FIG. 9E, and concentric circular micropillars on the Primary Dressing Surface are shown in FIG. 9F. In these figures, black micropillars represent silver nano-particles, grey micropillars represent zinc nano-particles, and white represents the perforation/thru-holes.

In one embodiment, there is disclosed a three-dimensional method of treating a wound, by using the enhanced wound care system described herein. The method comprises covering the wound with a primary dressing surface as disclosed herein, e.g., one comprising biocompatible and/or biodegradable polymer protuberances that are inserted into the wound to make direct contact with the wound.

PROPHETIC EXAMPLES

The disclosure described herein is not meant to be limited in scope by the specific prophetic examples disclosed. These prophetic examples are intended to be illustrative of the disclosure only and not wholly encompassing of it.

Prophetic Example 1

A Nano-Enhanced Wound Dressing according to the present disclosure may comprise a pattern of tapered PLGA micropillars on a perforated, conductive polymer Primary Dressing Surface. In this embodiment, each tapered micropillar may have a Base Diameter of 10 µm with a Height of 20 µm and a Spacing of 20 µm. In addition, each tapered micropillar may further comprise two different polymer layers, the first layer (nearest to the skin) containing a uniform distribution of 10 nm Silver nanoparticles and the second layer (furthest from the skin) containing a uniform distribution of 10 nm Zinc nanoparticles.

The micropillars may be fabricated using a rolling, thermo-compression or stamp, hot embossing technique wherein a mold master is temporarily pushed against the multiple PLGA layers under suitable conditions of pressure, temperature and time in order to cause the PLGA material to reflow and fill the conical depressions in said mold. Upon release there shall be tapered, dissolvable, nanoparticle-containing, polymer protuberances that, when brought into contact with the wound exudate, will exhibit an enhanced galvanic response with anti-microbial properties. And, as the PLGA micropillars dissolve away, additional silver and zinc will be controllably released into the wound.

Prophetic Example 2

A Nano-Enhanced Wound Dressing according to the present disclosure may also comprise a Woven Primary Dressing Surface onto which 5 mm Hexagon Islands of PEDOT are hot embossed. In this embodiment, each Hexagon Island further comprises multiple patterns of micropillars, with each separate pattern of micropillars further comprising PGSA polymer that contains a different medicinal specie nanoparticle. In this example, there are three possible different medicinal species of nanoparticles. The first is silver (10 nm), the second is Zinc (10 nm) and the third is Gold (10 nm). As the biodegradable PGSA dissolves away, three medicinal species will be released into the wound bed for enhanced and sustained anti-microbial action.

Prophetic Example 3

A Nano-Enhanced Wound Dressing according to the present disclosure may also comprise a molded PLGA Primary Dressing Surface onto which PGSA micropillars can be fashioned using photo-lithographic processes. In this embodiment, the PLGA primary dressing is made electrically conductive by virtue of the Silver nanoparticles immersed therein. This may be done when the molten PLGA material is pressed into the mold. Also found within the primary dressing surface of this embodiment, are thru-holes which allow moisture to pass. PGSA, a biodegradable/biocompatible/photosensitive polymer with Silver and/or Zinc nanoparticles immersed therein may be spun onto the primary dressing surface and illuminated with UV light through a contact mask. The mask contains tiny openings in the chrome where the location of pillars are desired. UV light passes through the mask and cures the PGSA in these locations only, whereas the unexposed PGSA may be dissolved away in subsequent development steps. Second and third rounds of spinning, exposing and developing cause secondary and tertiary micropillars to be formed with secondary and tertiary medicinal nano-particles held therein.

Claimed Embodiments from Priority U.S.
Provisional 61/956,479

The following 32 embodiments were claimed in the U.S. provisional application 61/956,479 which is incorporated herein by reference in its entirety for all purposes.

One aspect provides an enhanced wound-healing system comprised of one or more layers juxtaposed between a primary dressing surface and an outer cover wherein said primary dressing surface is further comprised of biocompatible and/or biodegradable polymer protuberances formed thereupon wherein each of said polymer protuberances is further comprised of medicinal nanoparticles infused therein and/or thereupon.

In one embodiment, the polymer protuberances are in the shape of a pillar with a base having dimensions on the order of 1 um to 100 um.

In one embodiment, the polymer protuberances have a cross-section shape that is: round, square, rectangular, hexagonal, elliptical or completely general.

In one embodiment, the medicinal nanoparticles infused within the polymer protuberances are selected from: silver, gold, copper, zinc, platinum, palladium and/or combinations thereof.

In one embodiment, the medicinal nanoparticles infused within the polymer protuberances are selected so as to facilitate galvanic action between said protuberances and the wound electrolyte.

In one embodiment, the medicinal nanoparticles are uniformly distributed within the polymer protuberances.

In one embodiment, the medicinal nanoparticles are non-uniformly distributed within the polymer protuberances so as to facilitate the optimal controlled release of anti-microbial and/or anti-biotic agents.

In one embodiment, the size, shape and spacing of the polymer protuberances are selected to maximize the contact area between said protuberances (i.e. electrodes) and the wound electrolyte for optimal galvanic response.

In one embodiment, the biodegradable polymer is selected from: PLA, PGA, PEG, PLGA and/or PGSA.

In one embodiment, the biocompatible polymer is comprised of PEDOT.

In one embodiment, the medicinal nanoparticles are spherical in shape with a diameter on the order of 5 nm to 100 nm.

In one embodiment, polymer protuberances devoid of any medicinal nanoparticles are instead coated with a medicinal layer.

In one embodiment, the medicinal nanoparticles are chosen to optimize the dissolution rate of different medicinal substances throughout the healing cycle.

In one embodiment, the primary dressing surface is a woven fabric.

In one embodiment, the polymer protuberances make the primary dressing surface superhydrophobic.

In one embodiment, the primary dressing surface is comprised of a perforated polymer.

In one embodiment, the primary dressing surface is comprised of perforated mylar, polyethylene, polypropylene, nylon, rayon and/or combinations thereof.

In one embodiment, the medicinal nanoparticles include anti-microbial, anti-fungal and/or anti-biotic agents.

In one embodiment, the medicinal nanoparticles are coated with anti-agglomeration agents.

In one embodiment, the polymer protuberances are activated (i.e. their medicinal constituents are released) as a result of some stimulus.

In one embodiment, one of more activation steps is carried out: activation by a saline rinse, activation by body temperature, activation by sweat or perspiration, activation by wound exudate and/or activation by magnetic means.

In one embodiment, a method of fabricating multiple-specie polymer protuberances on a primary dressing surface is provided whereby
  a first medicinal nanoparticle infused polymer layer is deposited onto the primary dressing surface
  a second medicinal nanoparticle infused polymer layer is deposited overtop of the first polymer layer
  a third medicinal nanoparticles infused polymer layer is deposited overtop of the second polymer layer
  a heated mold with a complementary pattern of pits is pressed against the primary dressing surface and the intervening multiple polymer layers to form a pattern of multiple-specie polymer protuberances.

In one embodiment, the first medicinal nanoparticle infused polymer layer is comprised of zinc nanoparticles in PLGA.

In one embodiment, the second medicinal nanoparticle infused polymer layer is comprised of silver nanoparticles in PLGA.

In one embodiment, the mold is made from silicon and includes a non-stick layer.

In one embodiment, the polymer protuberances are in the shape of a tapered cone.

In one embodiment, a method of fabricating single-specie polymer protuberances on a primary dressing surface is provided whereby
  a first medicinal nanoparticle infused polymer layer is deposited onto the primary dressing surface and uv light exposure through a first mask is done followed by development (removal) of the unexposed regions thereby resulting in a first pattern of single-specie polymer protuberances
  a second medicinal nanoparticle infused polymer layer is deposited onto the primary dressing surface and uv light exposure through a second mask is done followed by development (removal) of the unexposed regions thereby resulting in a second pattern of single-specie polymer protuberances different from the previous.
  a third medicinal nanoparticle infused polymer layer is deposited onto the primary dressing surface and uv light exposure through a third mask is done followed by development (removal) of the unexposed regions thereby resulting in a third pattern of single-specie polymer protuberances different from the previous.

In one embodiment, the biodegradable polymer is PGSA.

In one embodiment, the polymer protuberances are spaced apart on s scale that is compatible with the natural extracellular matrix.

In one embodiment, the first medicinal nanoparticle is silver.

In one embodiment, the second medicinal nanoparticle is zinc.

In one embodiment, the third medicinal nanoparticle is selected from any number of anti-microbial, anti-fungal, anti-biotic, germicidal and/or anti-bacterial agents.

In sum, the preferred embodiments and examples disclosed in the foregoing specification are used therein as vehicles of description, and not of limitation. There is no intention, in the use of such embodiments and examples to exclude any equivalents of the features shown and described, or portions thereof. It is appreciated that numerous modifications and/or embellishments to these embodiments and examples may be devised by those who are skilled in the art.

Therefore, it is understood that all such modifications and/or embellishments which fall within the spirit and scope of the present disclosure shall be covered by the following enumerated claims.

I claim:

1. An enhanced, wound care system comprising:
    one or more secondary dressing layers juxtaposed between a primary dressing surface and an outer cover;
    wherein the primary dressing surface comprises biocompatible and/or biodegradable polymer protuberances formed thereupon and arranged into certain preferred geometrical patterns;
    wherein each of said polymer protuberances further comprises medicinal nanoparticles embedded therein or thereupon;
    wherein, when said polymer protuberances are brought into contact with a wound, said medicinal nanoparticles are controllably released for purposes of accelerated healing of the wound; and
    wherein polymer protuberances with or without embedded medicinal nanoparticles are coated with a medicinal layer.

2. The enhanced wound care system of claim 1, wherein the polymer protuberances are in the shape of a pillar with a base having dimensions on the order of 1 um to 100 um.

3. The enhanced wound care system of claim 1, wherein the polymer protuberances are fashioned with a cross-section that is: round, square, rectangular, hexagonal, elliptical or some other preferred shape.

4. The enhanced wound care system of claim 1, wherein the medicinal nanoparticles are uniformly distributed along the length of the polymer protuberances.

5. The enhanced wound care system of claim 1, wherein the medicinal nanoparticles are non-uniformly distributed along the length of the polymer protuberances, so as to tailor their time rate of release.

6. The enhanced wound care system of claim 1, wherein the biocompatible and/or biodegradable polymer is selected from: PLA, PGA, PEG, PLGA, PGSA, PEDOT, and/or combinations thereof.

7. The enhanced wound care system of claim 1, wherein the polymer protuberances are designed to make the primary dressing surface superhydrophobic, superhydrophilic or somewhere in-between.

8. The enhanced wound care system of claim 1, wherein the primary dressing surface further comprises perforations or "weep" holes for purposes of moisture management.

9. The enhanced wound care system of claim 1, wherein the medicinal nanoparticles include: anti-microbial, anti-fungal, germicidal and/or anti-biotic agents, and optionally wherein the medicinal nanoparticles are approximately spherical in shape with a diameter on the order of 5 nm to 500 nm.

10. The enhanced wound care system of claim 1, wherein the polymer protuberances are activated (i.e. their medicinal constituents are released) as a result of some external stimulus, optionally, with activation by heat (body temperature), activation by chemistry (a saline rinse, sweat, perspiration) and/or activation by light, including electrical and/or magnetic means.

11. An enhanced, wound care system comprising:
    one or more layers juxtaposed between a primary dressing surface and an outer cover;
    wherein the primary dressing surface comprises biocompatible and/or biodegradable polymer protuberances formed thereupon and arranged into certain preferred geometrical patterns;
    wherein each of said polymer protuberances further comprises medicinal nanoparticles that are coated with a medicinal layer embedded therein or thereupon;
    wherein, when said polymer protuberances are brought into contact with a wound, said medicinal nanoparticles are controllably released for purposes of accelerated healing of the wound.

12. An enhanced, wound care system comprising:
    one or more layers juxtaposed between a primary dressing surface and an outer cover;
    wherein the primary dressing surface comprises biocompatible and/or biodegradable polymer protuberances formed thereupon and arranged into certain preferred geometrical patterns;
    wherein each of said polymer protuberances further comprises medicinal nanoparticles embedded therein or thereupon;
    wherein the primary dressing surface further comprises perforations or "weep" holes for purposes of moisture management;
    wherein, when said polymer protuberances are brought into contact with a wound, said medicinal nanoparticles are controllably released for purposes of accelerated healing of the wound.

* * * * *